(12) United States Patent
Shachar et al.

(10) Patent No.: US 8,323,270 B2
(45) Date of Patent: *Dec. 4, 2012

(54) ENHANCED METHOD FOR DELIVERING BEVACIZUMAB (AVASTIN) INTO A BRAIN TUMOR USING AN IMPLANTED MAGNETIC BREATHER PUMP

(75) Inventors: Yehoshua Shachar, Santa Monica, CA (US); Thomas C. Chen, La Canada, CA (US); Leslie Farkas, Ojai, CA (US); Bruce Marx, Ojai, CA (US); David Johnson, West Hollywood, CA (US); Laszlo Farkas, Ojai, CA (US)

(73) Assignee: Pharmaco-Kinesis Corporation, Inglewood, CA (US)

( * ) Notice: Subject to any disclaimer, the term of this patent is extended or adjusted under 35 U.S.C. 154(b) by 490 days.

This patent is subject to a terminal disclaimer.

(21) Appl. No.: 12/581,770

(22) Filed: Oct. 19, 2009

(65) Prior Publication Data

US 2011/0092960 A1 Apr. 21, 2011

(51) Int. Cl.
*A61K 9/22* (2006.01)
(52) U.S. Cl. .................................................. 604/891.1
(58) Field of Classification Search ............ 604/24, 604/891.1, 508, 506, 507, 509, 890.1; 600/2; 607/3, 60
See application file for complete search history.

(56) References Cited

U.S. PATENT DOCUMENTS

| | | | | | |
|---|---|---|---|---|---|
| 4,360,019 | A | * | 11/1982 | Portner et al. | 604/131 |
| 4,378,797 | A | * | 4/1983 | Osterholm | 604/24 |
| 4,610,658 | A | * | 9/1986 | Buchwald et al. | 604/9 |
| 5,429,582 | A | * | 7/1995 | Williams | 600/2 |
| 7,799,012 | B2 | * | 9/2010 | Shachar et al. | 604/508 |
| 7,799,016 | B2 | * | 9/2010 | Shachar et al. | 604/891.1 |
| 2004/0092577 | A1 | * | 5/2004 | Lerner et al. | 514/449 |
| 2007/0135765 | A1 | * | 6/2007 | Miller et al. | 604/131 |
| 2008/0064966 | A1 | * | 3/2008 | Brockway et al. | 600/486 |
| 2009/0143640 | A1 | * | 6/2009 | Saadat et al. | 600/104 |
| 2010/0004639 | A1 | * | 1/2010 | Pang et al. | 604/891.1 |

* cited by examiner

Primary Examiner — Nicholas Lucchesi
Assistant Examiner — Brooke Matney
(74) Attorney, Agent, or Firm — Marcus C. Dawes; Daniel L. Dawes

(57) ABSTRACT

A magnetically controlled pump is implanted into the brain of a patient and delivers a plurality of medicating agents mixed with Avastin at a controlled rate corresponding to the specific needs of the patient. The current invention comprises a flexible double walled pouch that is formed from two layers of polymer. The pouch is alternately expanded and contracting by magnetic solenoid. When contracted, the medicating agent Avastin is pushed out of the pouch through a plurality of needles. When the pouch is expanded, surrounding cerebral fluid is drawn into the space between the double walls of the pouch from which it is drawn through a catheter to an analyzer. In cases where a tumor resection is not performed, an intratumoral catheter will be implanted. Cerebral fluid drawn from the patient is analyzed. The operation of the apparatus and hence the treatment is remotely controlled based on these measurements and displayed through an external controller.

18 Claims, 21 Drawing Sheets

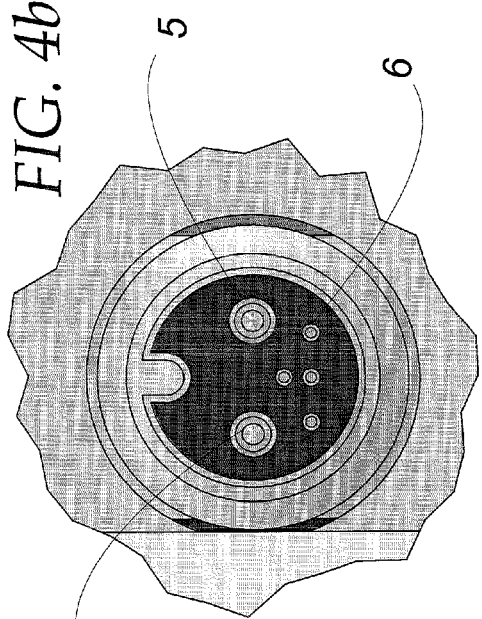
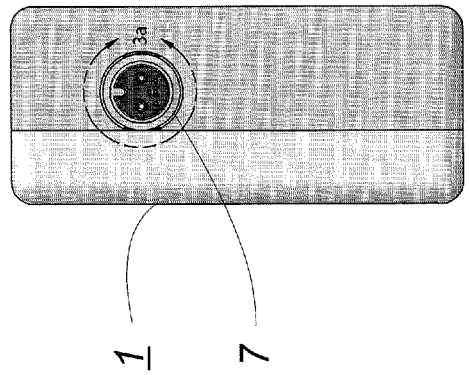
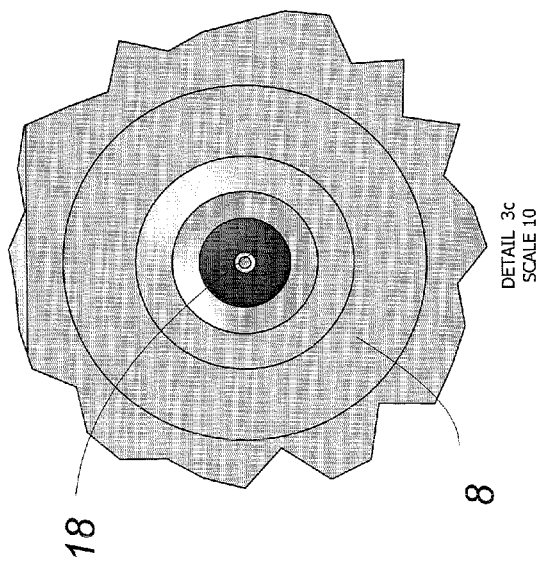
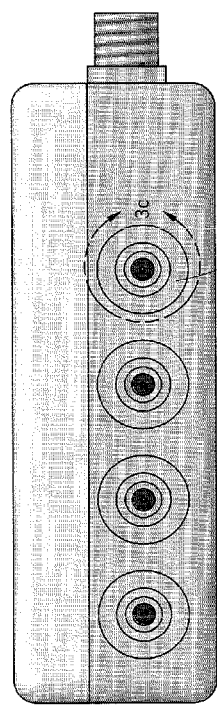
FIG. 4a
FIG. 4b
FIG. 4c
FIG. 4d

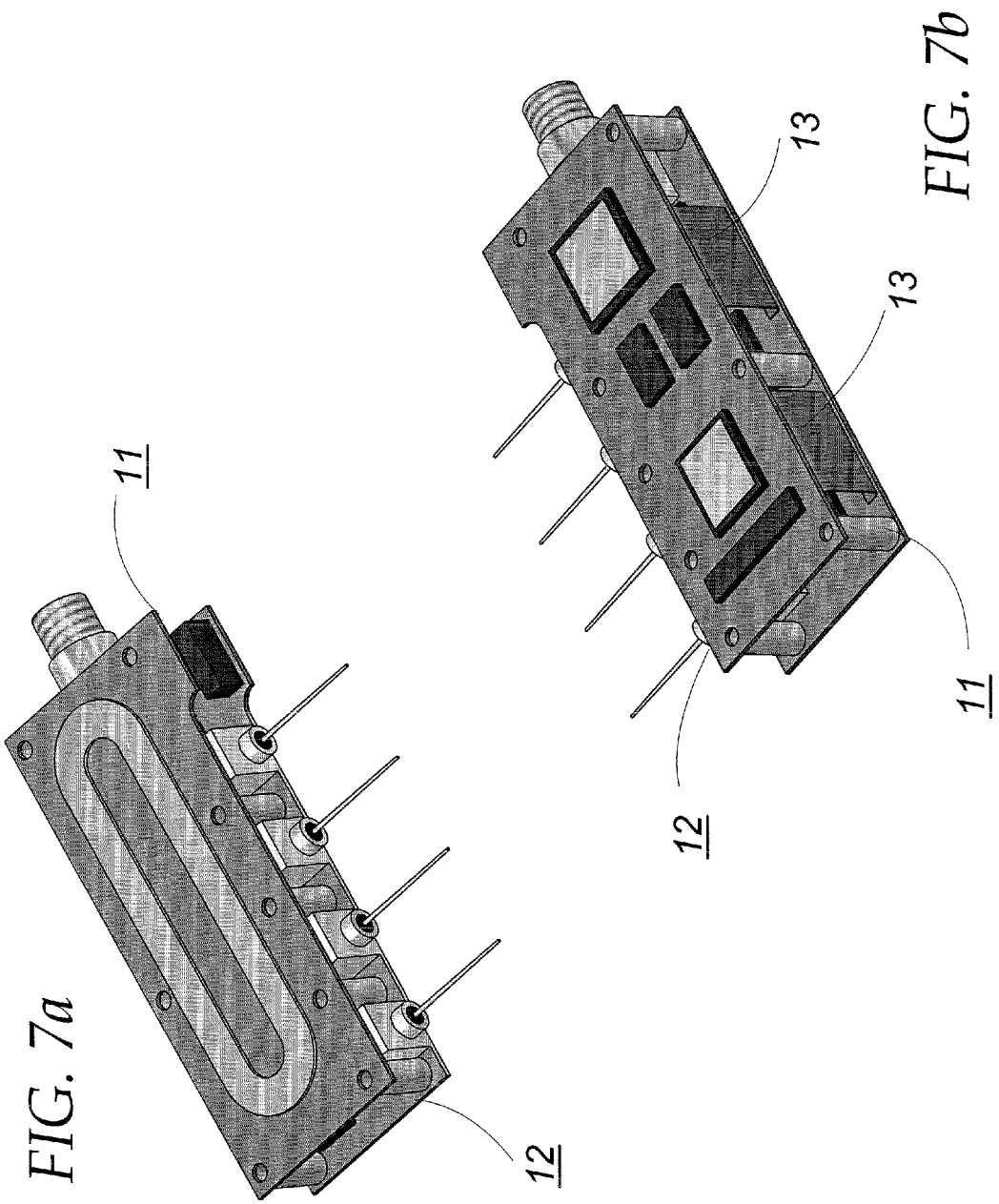

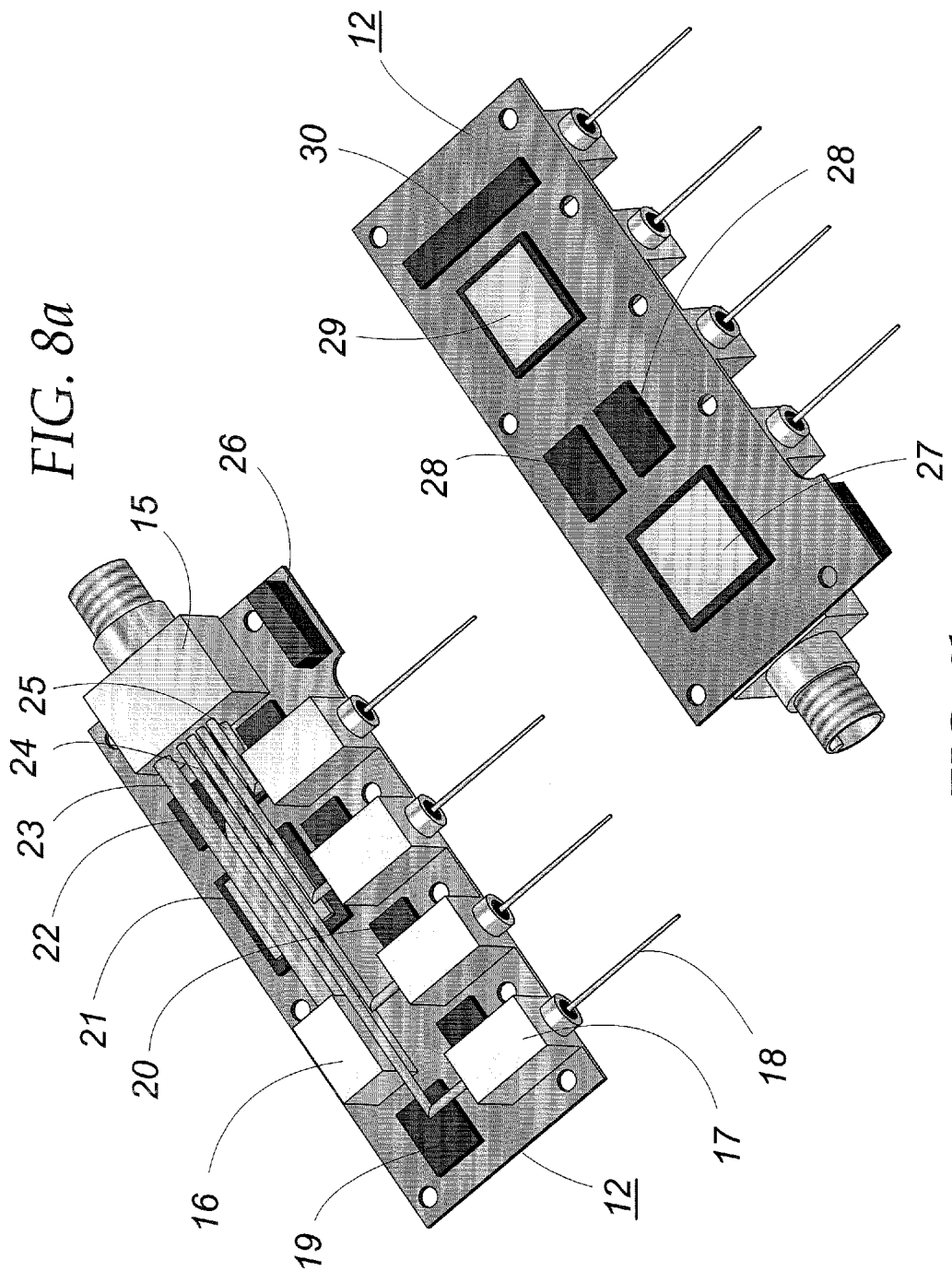

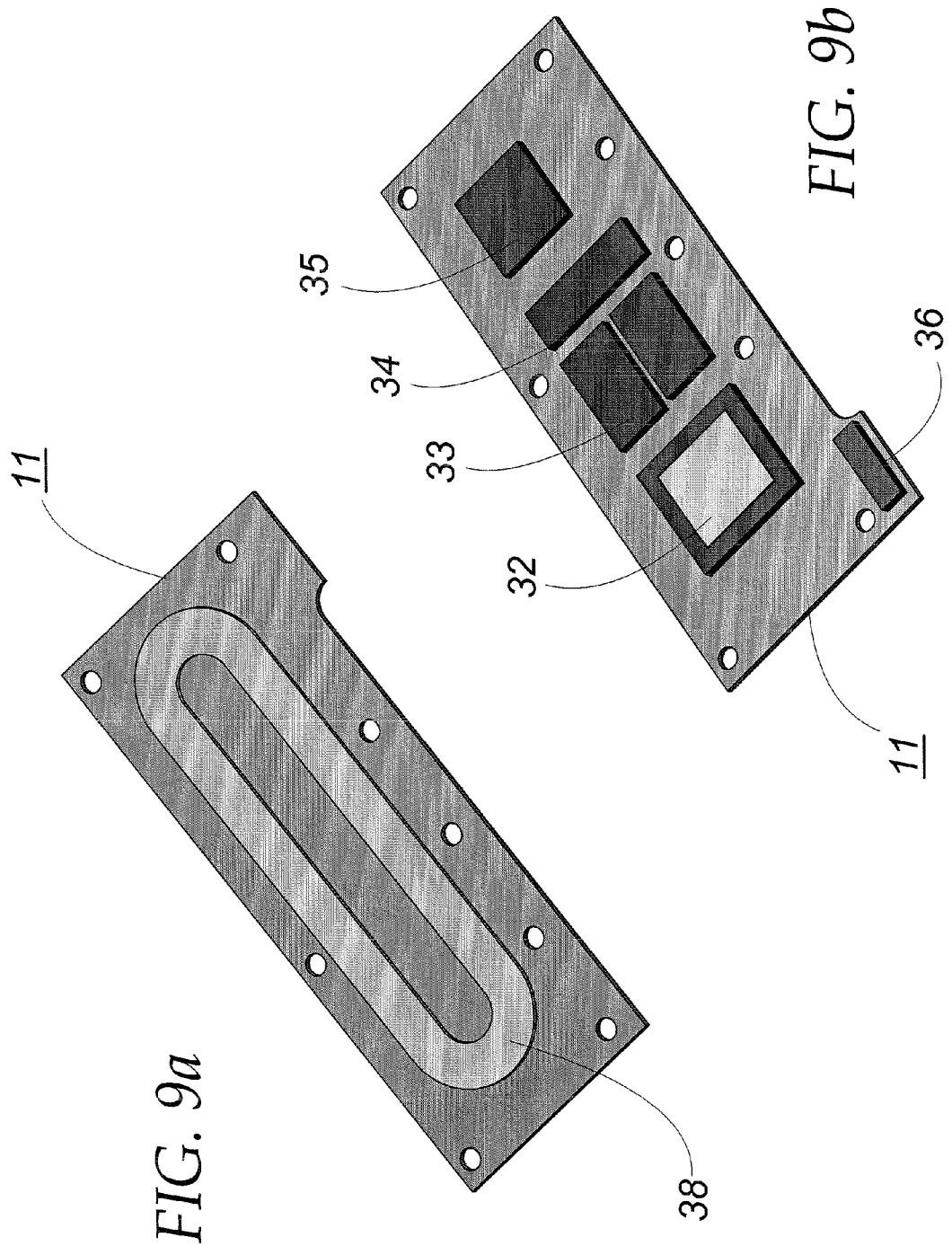

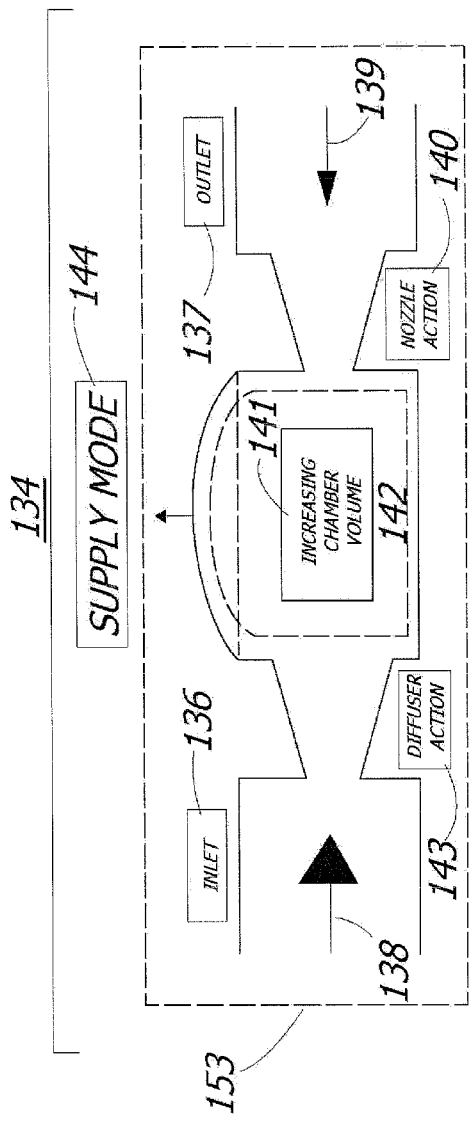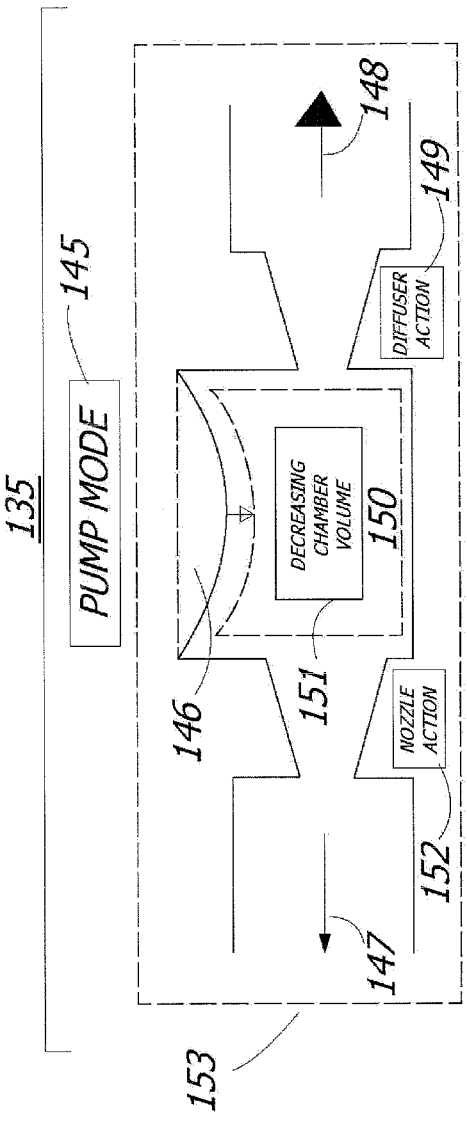
FIG. 10b
FIG. 10c

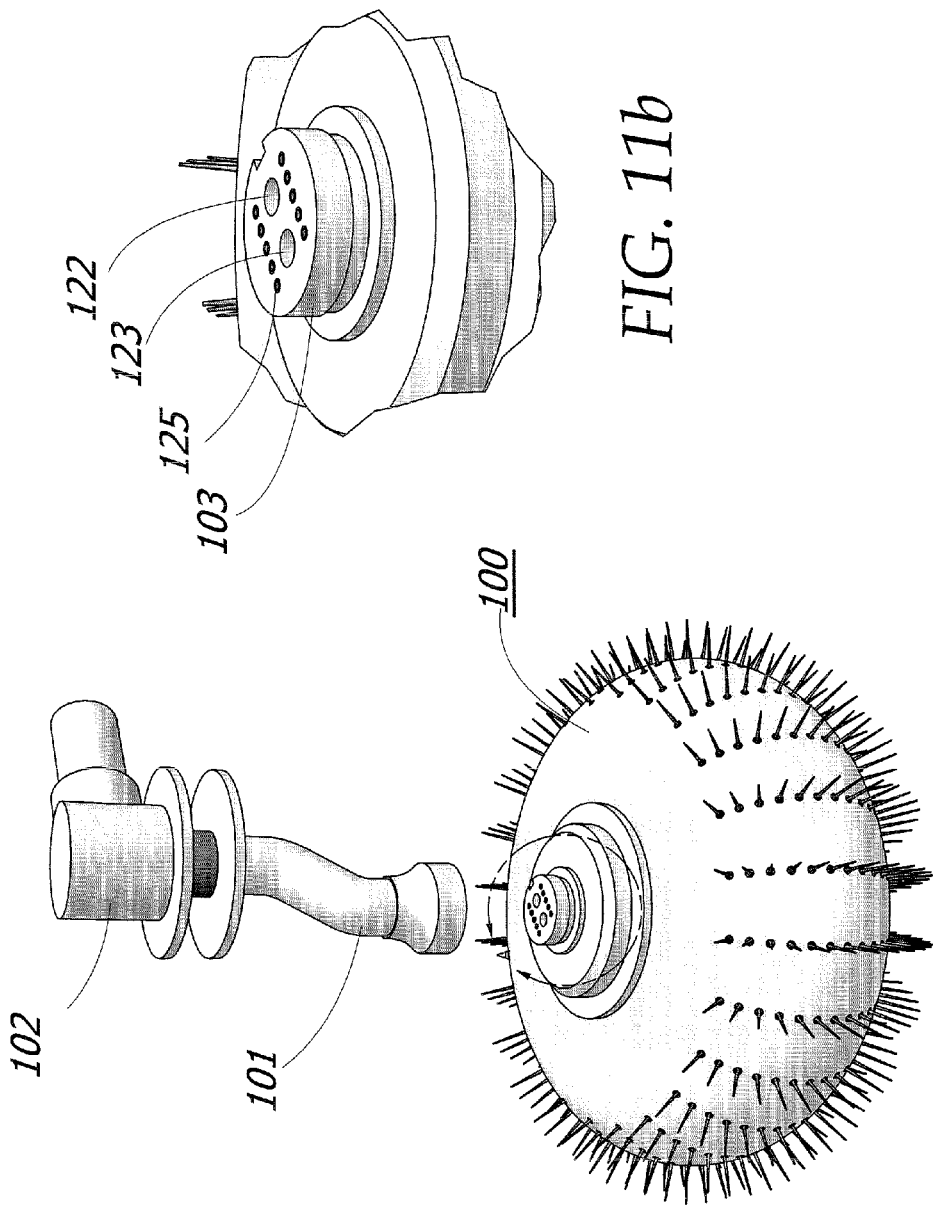

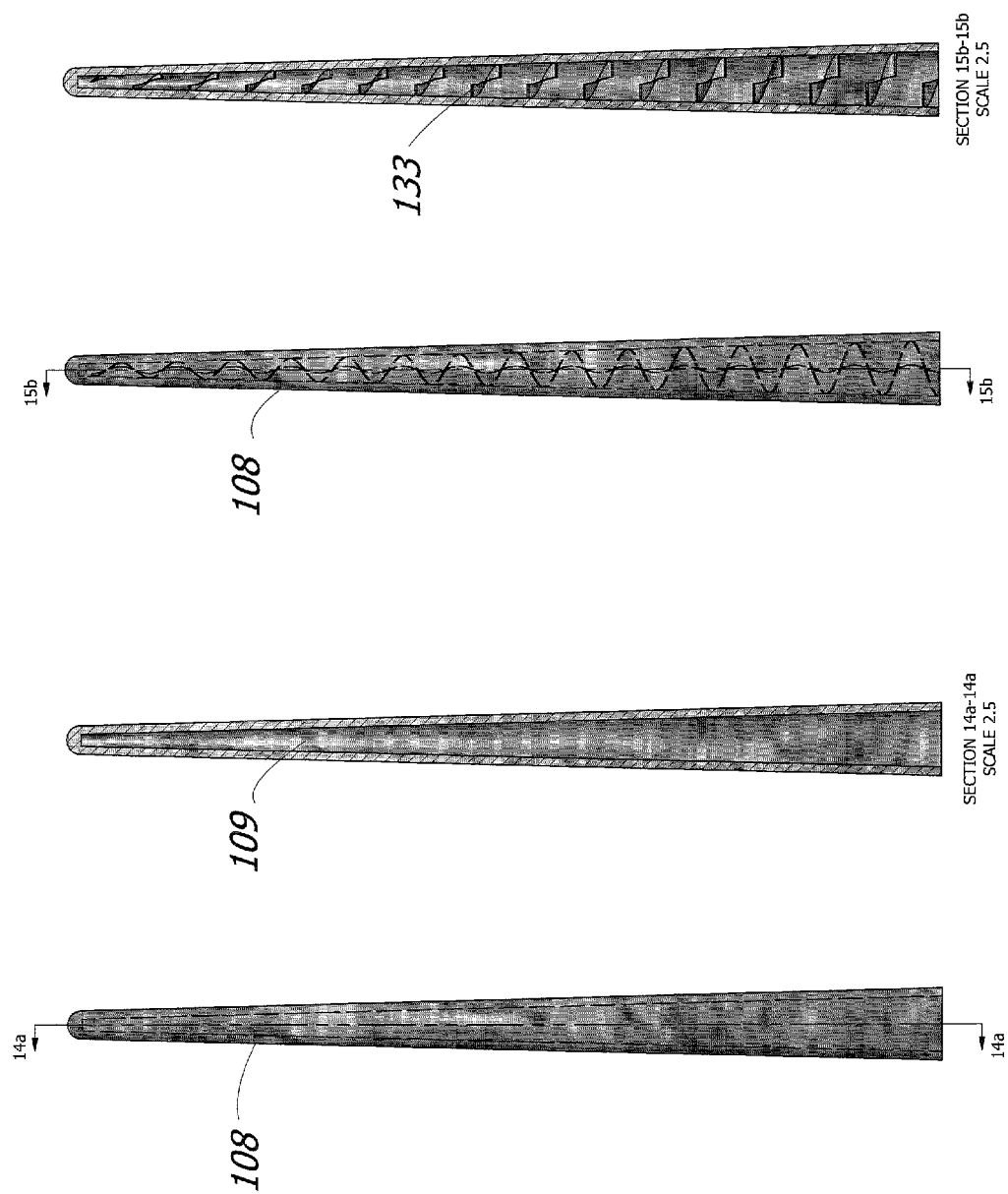

ENHANCED METHOD FOR DELIVERING BEVACIZUMAB (AVASTIN) INTO A BRAIN TUMOR USING AN IMPLANTED MAGNETIC BREATHER PUMP

BACKGROUND OF THE INVENTION

1. Field of the Invention

The invention relates to the field of implantable drug delivery systems, specifically a magnetically controlled aspirating pump and a method for delivering the anti-angiogenesis agent Bevacizumab (Avastin) into a brain tumor using the same.

2. Description of the Prior Art

When tumors develop inside the human body, the options for available treatment are fairly narrow. This is even more so when the tumor develops inside a vital organ such as the brain. Diseases such as brain cancer, i.e. malignant gliomas, and other cancers that develop in or around the brain are notoriously difficult to treat and thus have a high mortality rate. The invention described herein is directed specifically for malignant gliomas; however, it is applicable to all types of malignant tumors where local control is desired with direct intratumoral treatment with Avastin.

Traditionally, the options for treating a tumor located in or on the brain include surgery, radiation, chemotherapy, and local intratumoral therapy. Each of these prior methods of treating a brain tumor have had some form of success in the past, however each of them also contain various deficiencies and pitfalls that make them less than ideal when treating a patient. What is needed is a more reliable, easier, and effective process for treating a malignant brain tumor.

The oldest and most direct way for treating a brain tumor is to remove it surgically. Surgery is effective in obtaining tissue diagnosis and removing the mass effect of the tumor from the adjacent normal brain. However, it is invasive, expensive, and poses potential surgical complications for the patient. Most importantly, surgery cannot cure a malignant brain tumor, as the cancer cells have often invaded far into the normal brain when the diagnosis is first confirmed. Additionally, surgery is only available when the tumor is in a surgically accessible location. Tumors located deep within the brain are often inoperable as the surgery would significantly impair the patient's neurological function. Even if surgery is possible, there is still a chance of brain damage and an extremely long recovery time associated with surgery.

Radiation is the next mode of treatment for brain cancer. It is usually given as a fractionated dosage treatment, covering a certain field encompassing the tumor, over a period of six weeks. Spatially localized forms of radiation, including cyberknife and gamma knife have been used with varying levels of success. Although radiation is still widely acknowledged as the most effective mode of adjunctive treatment for a malignant brain tumor, it suffers from the disadvantage of limited fractions and applications, as the brain can only be radiated so much without developing severe sequelae.

The third method used to combat brain tumors is systemic chemotherapy. Systemic chemotherapy is a viable option as an adjunct to radiation and surgery. However, it is limited in efficacy in brain cancers by: 1) delivery across the blood brain barrier, 2) development of drug resistance by the cancer cells, and 3) systemic side-effects from the chemotherapeutic agent. Because the blood brain barrier is only partially broken down in the presence of a malignant brain tumor, it still impairs the effective delivery and transport of systemic chemotherapy into the brain cancer. Secondly, brain tumors can develop drug resistance. As a result, the cancer learns how to avoid cytotoxicity of the delivered drug. Lastly, chemotherapy is distributed systemically throughout the entire body. Because the whole body of the patient undergoes the treatment (not just the tumor and the tumor related area), undesirable side effects such as nausea, diarrhea, hair loss, and loss of appetite and energy may occur. Some of the side effects are so strong in some patients that chemotherapy is unavailable to them as a treatment and thus decrease their overall chances for survival.

The anti-angiogenesis agent Avastin is currently FDA approved for the treatment of recurrent glioblastoma multiforme (GBM). It is an antibody which is capable of binding to vascular endothelial growth factor (VEGF), the angiogenesis agent secreted by glioma cells, and is responsible for binding to the endothelial cells in the glioma, causing the blood vessels to proliferate and vascularize the glioma. It is currently administered via intravenous administration every two weeks, and is given as a stand-alone drug. No clear benefit has been documented for combination of Avastin with standard cytotoxic chemotherapy ie irinotecan (CPT-11). Because of the anti-angiogenesis nature of Avastin, it would be more effective when given on a continuous metronomic delivery. However, because of its need for intravenous administration, it is impossible to deliver it on a continuous basis. Moreover, because Avastin is an antibody, it is not capable of effectively crossing the blood brain barrier. Instead, it only binds to the VEGF present in the luminal side of the blood vessel. Intravenous Avastin is associated with a number of systemic side-effects including poor wound healing, deep venous thrombosis, renal toxicity, and threat of intracerebral hemorrhage. On the other hand, intratumoral Avastin would not be affected by these systemic complications, including poor wound healing.

The last major method of treating brain tumors has been the application of various local intratumoral therapies. These therapies include chemotherapy wafers, stereotactic injections, and convection enhanced deliveries. All of these treatment therapies involve directly infusing the tumor with an appropriate drug regimen; however this method too is not without its limitations. Chemotherapy wafers (Gliadel) are currently limited by only one drug available (BCNU), and by its diffusion capability of only a few millimeters away from the tumor bed. Stereotactic injections of chemotherapy have also been applied. However, only one injection is available at any single time. If another injection is needed, then another stereotactic surgical injection would have to be performed. Moreover, the spread of the chemotherapy is limited to the injection site and some of the adjacent normal brain. Lastly, convection enhanced delivery via an external micropump has been used to increase the circumference of drug delivery. It is usually given by an externalized catheter, and the drug is delivered for a cycle of 4-6 days. At the end of that time, the catheter will have to be removed. If the drug is to be delivered again, another surgical procedure for convection enhanced delivery will have to be performed. This can be very expensive and painful as some intratumoral therapies involve exposing the brain to an externalized catheter for long periods of time or complicated implantations of temporary catheters and other medical devices. Additionally, many of the previous intratumoral therapies are ineffective and do not significantly enhance or lengthen the life of a patient receiving such treatment.

The underlying hypothesis of using polypharmacy employed by the current invention is based on the premise that combination therapy is often better than monotherapy. Thus, a first step in administrating a cytotoxic agent is to determine the maximum tolerated dose (MTD). However, when used in traditional treatment mores, such as chemotherapy, the cytotoxic agents are delivered to the patient in a manner that allows the cytotoxic agents to be distributed more or less globally throughout the body of the patient. Relatively large doses of the drugs are required since only a small fraction of the administered dose will be present at the tumor site at any given time. The remainder of the dose will be in the other parts of body. Moreover, a major problem with conventional chemotherapy is lack of specificity in targeting the cancer cell.

The use of large doses of toxic agents often leads to serious and debilitating side effects. Moreover, the global administration of drugs is often not compatible with combination therapies where a number of medicating agents are used synergistically to treat tumors or other conditions. Thus, the global administration of medicating agents to treat tumors and other such medical conditions is an inefficient and often dangerous technique that often leads to severe or debilitating side effects.

The use of intratumoral Avastin has never been used in the human population. Considerations of intracerebral hemorrhage and lack of an effective delivery device have been factors inhibiting its use. From a treatment standpoint, intratumoral Avastin does have the advantage of continuous metronomic delivery, delivery to the glioma cells that are actually secreting VEGF (not just the luminal side of the blood vessel as in intravenous delivery), and potentially much lower amounts of Avastin needed to be effective. Recent experiments performed demonstrated that Avastin does not induce an intracerebral or intratumoral hemorrhage when administered intratumorally in an intracranial rodent model. Moreover, there was no increased evidence of an immune response from infusion of an antibody such as Avastin. Most importantly, we demonstrated that the survival time of these animals was significantly prolonged with intratumoral Avastin compared to intravenous Avastin as seen in FIG. 18.

Local administration of an anti-VEGF antibody has been employed by Roche (formerly Avastin) for macular degeneration. Studies have shown that it may be administered safely locally. However, intratumoral delivery of Avastin has never been shown in either in-vivo animal studies or human studies.

Recently, there have been some developments in the field of medical drug delivery systems. The majority of these systems have taken the form of a pump or other device that releases a variety of drugs into various positions in and around the body of a patient.

For example, many of the devices found in the prior art are much like the inventions disclosed in U.S. Pat. No. 6,852,104 ("Blonquist") and U.S. Pat. No. 6,659,978 ("Kasuga"). Both of these inventions comprise a small tank for holding a drug regimen, a pump for pumping the drug regimen into the body of a patient, and some sort of electronic control system that allows the user to program the specific amount and at what time a certain drug regiment is to be administered. While these apparatus may be ideal for administering certain drugs such as insulin to patients who are diabetic, they are neither designed nor suitable for directly treating a tumor within the brain of a patient.

Other prior art examples such as U.S. Pat. No. 5,242,406 ("Gross") and U.S. Pat. No. 6,571,125 ("Thompson") offer smaller, more convenient alternatives for administering drugs, however their reliance on maintaining a specific set of pressures and a certain amount of electrical current respectively makes them too complicated and prone to error.

U.S. Pat. No. 7,351,239 ("Gill"), U.S. Pat. No. 7,288,085 ("Olsen"), and U.S. Pat. No. 6,726,678 ("Nelson") disclose a pump or reservoir that is capable of delivering medicating fluids to the brain, but requires that the pump and drug reservoir be implanted in different locations within the patient. This configuration is not only uncomfortable for the patient, but also increases the possibility of infection and unnecessarily complicates the implanting procedure. Additionally, every time the patient needs the drug reservoir refilled or the pump battery replaced, the physician must invasively re-enter the patient. Finally, none these prior methods disclose a way of measuring the value of the vascular endothelial growth factor (VEGF) so as to enable tailoring of the delivered medical agent, toxicity to meet the needs of a specific individual patient.

What is needed is a device and a method that is capable of delivering medicating agents directly to a tumor located in the brain of a patient that is easy to operate and relatively simple to implant, while at the same time, is easy to maintain throughout the patient's treatment cycle and customize to the patient's specific needs without causing all of the negative side effects associated with previous treatment methods.

The combination of Avastin with the MBP allows for an unique combination of drug and device, enabling a new combination to be used in the treatment of malignant gliomas.

BRIEF SUMMARY OF THE INVENTION

A magnetically controlled pump is implanted into the brain of a patient and delivers a dose of Avastin at a controlled rate corresponding to the specific needs of the patient. The current invention comprises a flexible double walled pouch that is formed from two layers of polymer. The pouch is alternately expanded and contracting by magnetic solenoid. When contracted, Avastin is pushed out of the pouch through a plurality of needles. When the pouch is expanded, surrounding cerebral fluid is drawn into the space between the double walls of the pouch from which it is drawn through a catheter to an analyzer. Cerebral fluid drawn from the patient is analyzed. The operation of the apparatus and hence the treatment is remotely controlled based on these measurements and displayed through an external controller.

The illustrated embodiment of the invention solves the above limitations in the prior art and other problems by effectively treating brain tumors using a magnetically controlled pump implanted into the tumor resection cavity or a multi-delivery catheter implanted into an unresectable tumor, i.e. a tumor in which a surgical removal of all or part of an organ, tissue, or structure is not practically feasible. Through both proximal ports, an internalized externally controlled pump will deliver up to four different kinds of chemotherapeutic agents, including the drug Avastin, at a controlled rate corresponding to the specific needs of the patient.

The microdelivery pump has three components: a proximal head implanted into the tumor, a catheter extending from the proximal head, and an analyzer unit connected to the catheter. The proximal head is either comprised of a catheter inserted into the tumor or a magnetic breather pump. Which type of proximal head is employed depends on whether a tumor cavity is available. If a tumor is considered unresectable or if the patient does not want open surgery, only a catheter only will be implanted. However, if a resection is performed, then different size magnetic breather pumps can be inserted into the tumor cavity, depending on its volume. The entire unit is self-contained and entirely internalized.

Briefly, the illustrated embodiment of the invention comprises a proximal delivery device which will be implanted into the patient's brain tumor. A first embodiment is made for patients who have had a surgical resection, with a resultant tumor cavity. In those cases, a small, round flexible pouch that is formed from two layers of polymer material is implanted.

At the head and base caps of the pouch are electromagnetic coils that, when activated, are alternately attracted and repelled from each other thus causing the pouch to contract and expand. The inner layer of polymer material acts as a reservoir for Avastin or a mixture of several medicating agents including Avastin. The inner layer also contains a plurality of polymer needles on its surface that allow the medicating agent to pass through the outer polymer layer and deep into the surrounding tissue of the patient, when the pouch is contracted by the electromagnetic coils. The outer polymer layer is porous which allows surrounding cerebral fluid to be drawn into the pouch from the suction that is created when the pouch is expanded by the electromagnetic coils. This mechanical aspiration and exchange of fluids by the pouch is then repeated until the entire amount of Avastin has been delivered, or until a preselected time period has expired.

The head cap of the pouch also contains a valve that allows the reservoir of the apparatus to be refilled and for cerebrospinal fluid that has been drawn into the pouch to be withdrawn from the cranium of the patient via a suction nozzle. In this way, the pump also enables a decompressive mechanism for controlling the intratumoral pressure, and for sampling fluid.

In patients in whom a resection cannot be performed, an alternative embodiment of the current invention involving a multidelivery catheter is employed. Conventional catheters used for convection enhanced delivery for brain tumors consist of either a single port in the tip of peritoneal tubing used for ventriculoperitoneal shunts, or a proximal shunt catheter with multiple holes cut within 1 cm of the tip of catheter tip. The multidelivery catheter described herein is comprised of a catheter tip from which a balloon with multiple spines emerges under positive pressure from the pump.

The medication intake line and the cerebrospinal fluid return line coupled to the head cap of the apparatus are housed within a silicone catheter. The catheter runs underneath the scalp of the patient, around the back of the head, and emerges from the patient in an easily accessible location such as beneath the head of the clavicle as in a Port-A-Cath. The catheter is coupled to an analyzer unit, thus coupling the aspirating pump to a control device and forming a drug delivery system.

The analyzer unit is a housing means for several key components of the apparatus. Cerebrospinal and/or tumor fluid that has returned from the patient passes through a lab-on-a-chip which measures and monitors the vascular endothelial growth factor (VEGF) levels for indications of progress or regression of the patient's tumor burden. The user or physician operating the apparatus can then adjust or change the drug regimen the patient is receiving based on these measurements. Also coupled to the unit are four piezo pumps that send up to four different medicating agents, one of which being the drug Avastin, through the catheter and into the reservoir of the implanted pouch. A Blue Tooth® chip also allows the unit to be controlled by a physician from a remote location. Flash memory chips and an artificial intelligence processor complete the circuitry needed in order to provide the patient with an effective, easy to use apparatus that delivers medicating agents at a set and controlled rate. Finally, the analyzer unit or chemotherapy pumping device (CPD) includes a long lasting lithium ion battery that powers the unit itself.

It is therefore an object of the invention to provide a patient with constant medication without re-implanting a catheter every time a patient needs to be treated.

It is another object of the invention to provide a metronomic continuous delivery of a medicating agent.

It is a further object of the invention to provide users and physicians in charge of a patient's treatment instant monitoring and feedback of various tumor parameters in order for the patient's treatment to be changed or adjusted accordingly.

It is a further object of the invention to provide patients with brain tumors an effective way of treating their affliction while minimizing the side effects of chemotherapy.

Another object of the invention is to enhance the mechanism of vectorial change of tumor escape mechanism by introducing a sufficient tumor antigen to stimulate the immune system of the patient.

Another object of the invention is to assist in irrigating the solid tumor by increasing cell adhesion molecules which are used for the adherence of cytotoxic cells to target cells before lysis can ensue. The malignant cells cannot bind to cytotoxic cells. The use of the apparatus will improve and enhance such a process.

Yet another object of the invention is to administrate biological response modifiers (BRMs) with an improved dose, local delivery and scheduling on a case-specific basis using the programmable microcontroller and its associated valve mechanism.

Another object of the invention is to allow the clinician the ability to prescribe an optimal biological dose (OBD) of Avastin as opposed to maximum tolerated dose (MTD) of Avastin by the use of an apparatus control mode defined by its programmability and its logic, which is embedded in microcontroller look-up-tables.

Another object of the invention is to incorporate the pharamacokinetic and pharmacodynamic parameters associated with chemotherapeutic agents so as to achieve the desired results without the toxic side effects known to those familiar with the art.

Another object of the invention is to modulate and modify the output of the Avastin during treatment by changing the procedure in real time through the use of the command structure of the microcontroller look-up-tables with the use of a communication link built into the apparatus.

Another object of the invention is to regulate the rate of dispensation of the Avastin by modifying the duty cycle of the valve located in the apparatus.

Another object of the invention is to regulate the intake of the tumor BRMs due to their pleiotropic nature, and allow for processes and mechanisms to develop by reducing or enhancing the various agents in the medicating apparatus (MBP), hence providing a treatment specific to the patient (e.g. tumor, size, lysis, etc).

Another object of the invention is to provide the clinician a way to allow the expression of BRMs cascade effects (due to the communication of cytokines as messengers with their synergistic, additive or antagonistic interactions that affect the target tumor cells).

Another object of the invention is to provide scheduling of medicating agents such as cyotototoxic chemotherapy, BRMs, and Avastin as based on their toxicity, and to allow for measures such as bioavailability, solubility, concentration, and circulation based on locality, both of which are the improved approach to the elimination of solid tumors.

Another object of the invention is to address the individual differences of various tumors based on the disease stage, immune factors, body weight, age and chronobiology through the ability of the apparatus to locally administer the agents, dosing, and scheduling.

Another object of the invention is to provide an effective mode of administrating BRMs with chemotherapy as a combination therapy by making available a local administration of different IFNs with IL-2 or IL-2 in combination with monoclonal antibodies and tumor necrosis factors (TFNs), and scheduling by the use of the invention under metromonic regiment.

Another object of the invention is to enable drug manufacturers to evaluate the effectiveness of its drug during animal and clinical studies by providing the details and feedback on the use, dose, cycle, circadian time effects and the entire pharmacokinetic and pharmacodynamic behavior of the medicating agents not as verbal reports of symptomalogy chronicles by the patient, but as a biological measure of tumor responses to the agents.

Another object of the invention is to provide a method and apparatus for local administration of BRMs, cytotoxic chemotherapeutic agents, and Avastin, to enhance mechanisms that support overlapping effects in reducing tumor burden and elimination of tumors. To induce an improved response by the use of biomodulators (augmenting the patient's anti-tumor response via production of cytokines), decreasing suppressor mechanisms, increasing the patient's immunological response, limiting the toxicity of such agents (by the locality), maximizing the dose, increasing susceptibility of cells membrane characteristics for improved chemotherapy results at the site, and decreasing the tumor's, ability to metastasize.

The above characteristics are measurable elements since dosing and scheduling improves the effectiveness of chemotherapy on malignant cells and reduces the exposure of such toxins to normal tissues. One embodiment provides improved immunomodulation with relatively little immuno-suppression.

Another object of the invention is to provide for defining an improved dose and schedule of biological agents to maximize the anti-tumor effects of each agent while not increasing toxicity to the patient. Treatment modality by the use of combination therapy and local administration of such agents on a specific schedule is one of the benefits of the invention.

It is yet another object of the invention to provide operating physicians a method of treating brain tumors without having to worry about Avastin being diluted or hindered by the blood brain barrier (i.e. direct antibody injection into the tumor).

Finally, it is yet another object of the invention to provide preoperative simulation of the infusion of Avastin and other intratumoral infusates to maximize infusion efficiency and minimize local toxicity to the adjacent brain from leakage of the infusate into the normal tissue. The diffusion model permits a systematic design of targeted drug delivery into the human brain by predicting achievable volumes of distribution for therapeutic agents based on the established transport and chemical kinetics models. The model can be simulated in a computer-aided brain analysis before the actual placement procedure, thus reducing the need for trial-and-error animal experimentation or intuitive dosing in human trial, maximizing preoperative planning, and minimizing intraoperative and postoperative complications.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 4a is a right side view of the CPD highlighting the delivery connector.

FIG. 4b is a magnified view of the delivery connector of FIG. 4a.

FIG. 4c is a bottom view of the CPD with an ampoule bay highlighted.

FIG. 4d is a magnified view of an ampoule bay of FIG. 4c.

FIG. 7a is a perspective view of the top of the induction charger assembly and pump electronics assembly coupled together.

FIG. 7b is a perspective view of the bottom of the induction charger assembly and pump electronics assembly coupled together.

FIG. 8a is a perspective view of the top of the pump electronics assembly.

FIG. 8b is a perspective view of the bottom of the pump electronics assembly.

FIG. 9a is a perspective view of the top of the induction charger assembly.

FIG. 9b is a perspective view of the bottom of the induction charger assembly.

FIG. 10b is a diagram which depicts the "electrostatic muscle" defining the "supply mode" of the implantable cranium pump.

FIG. 10c is a diagram which depicts the "electrostatic muscle" defining the "pump mode" of the implantable cranium pump.

FIG. 11a is an isometric view of the implantable cranium pump with the pump-to-seal interconnect disconnected.

FIG. 11b is a magnified view of the pump head assembly.

FIG. 13b is a magnified view of the injector spines in the circled region 13a of FIG. 13a.

FIG. 14a is a side and cross sectional view of a hollow injector needle.

FIG. 14b is a side and cross sectional view of a spiral injector needle.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DEFINITIONS

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the methods, devices, and materials are now described. All publications mentioned herein are incorporated herein by reference for the purpose of describing and disclosing the materials and methodologies which are reported in the publications which might be used in connection with the invention. Nothing herein is to be construed as an admission that the invention is not entitled to antedate such disclosure by virtue of prior invention.

The following mathematical symbols used here in refer to its definitions as follow: Q is infusate flow rate; $\rho$ is fluid density; $\vec{v}_f$ is fluid velocity vector in the catheter; $\mu$ is fluid viscosity; $\epsilon$ is tissue porosity; p is infusion fluid pressure; $\vec{\nabla}p$ is pressure gradient; $D_b$ is bulk diffusivity; $D_e$ is effective diffusion tensor; $C_f$=Concentration of drug; $\vec{v}_t$ is flud velocity in the porous tissue; $D_e$ is mean effective diffusivity; k is first order rate constant accounting for drug reaction; $\mathfrak{R}$ Hydraulic conductivity tensor, which is a function of fluid viscosity $\mu$ and effective tissue permeability tensor $\kappa$; $\vec{v}_t \cdot \vec{\nabla} C_t$ is convection term; $D_e \vec{\nabla} C_t$ is diffusion flux; $C_t(\vec{x}, t)$ is tissue averaged species concentration; $R(C_t, \vec{x})$ is drug decomposition due to metabolic reaction; and $S(C_t, \vec{x})$ is sink term due to bio-elimination.

DETAILED DESCRIPTION OF THE PREFERRED EMBODIMENTS

The apparatus is additionally described and disclosed within U.S. patent application Ser. No. 12/143,720 filed Jun. 20, 2008, which is herein incorporated by reference in its entirety.

Figure 10A:
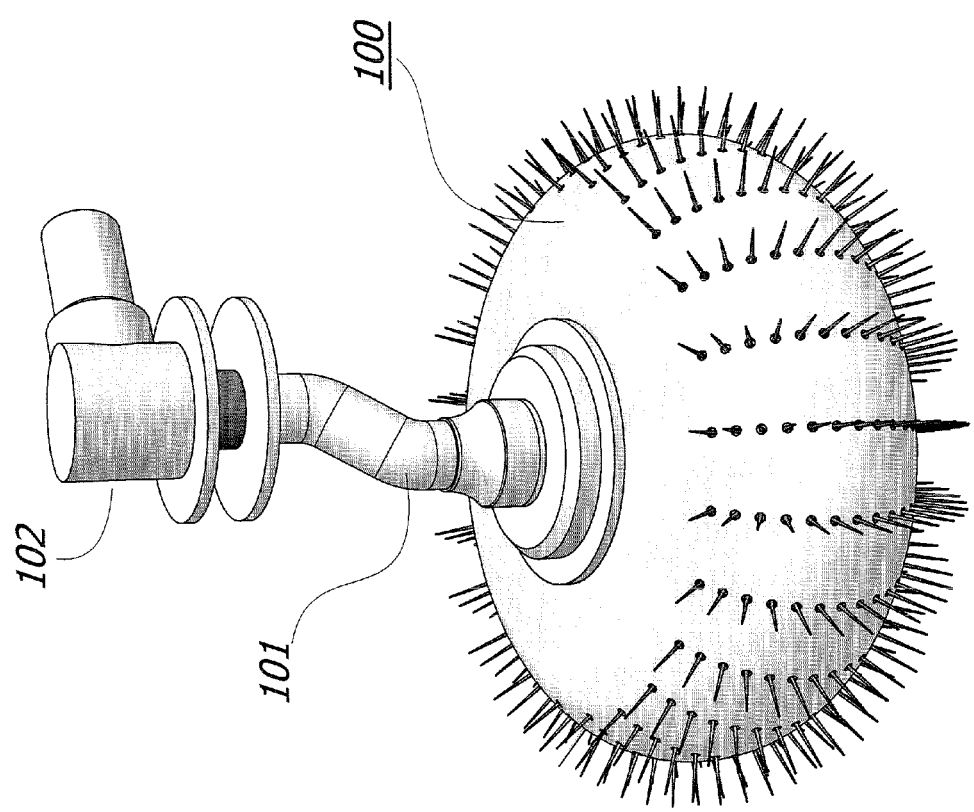
FIG. 10a is an isometric view of the implantable cranium pump.
Figure 12:
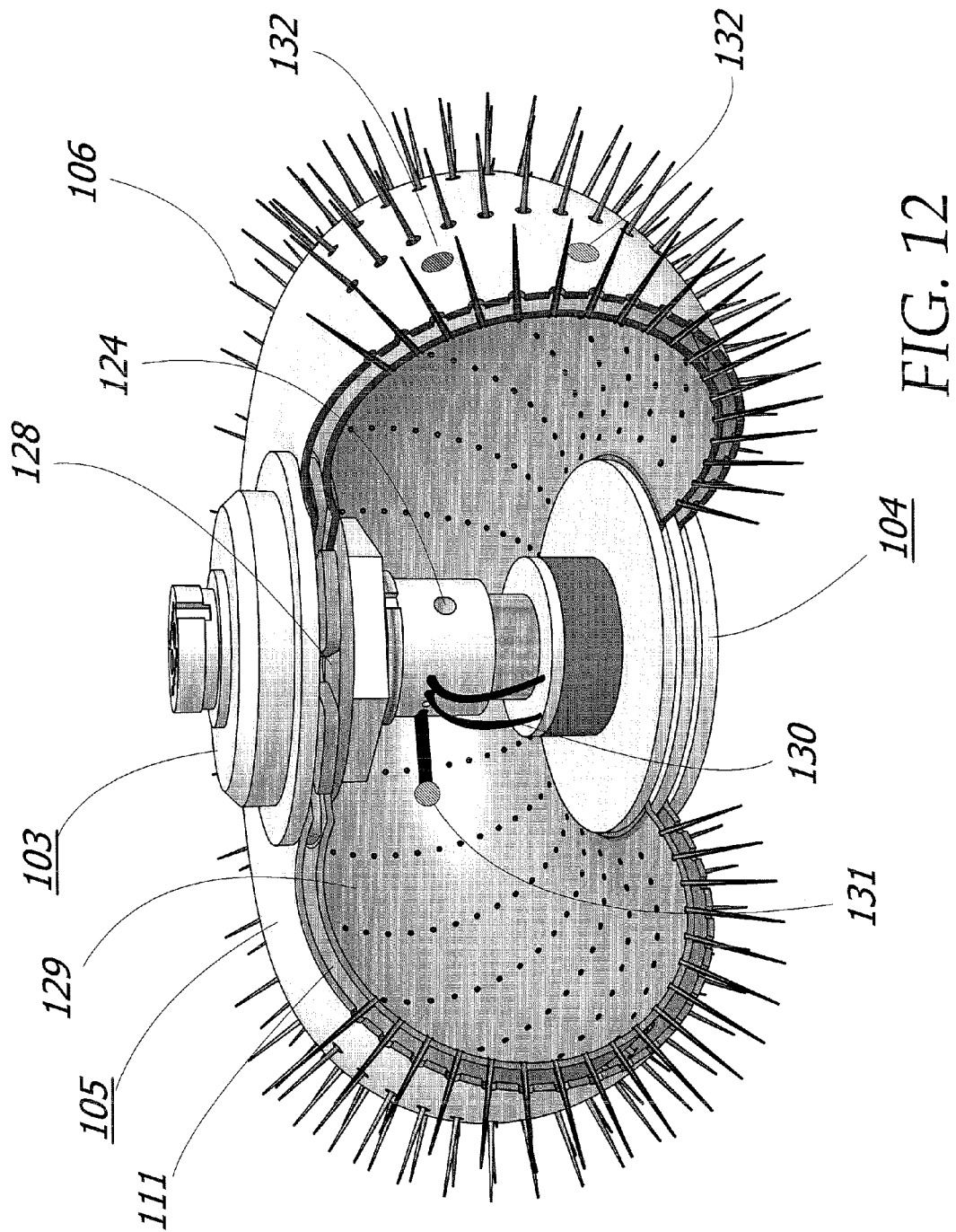
FIG. 12 is a cross sectional view of the implantable cranium pump.
Figure 13C:
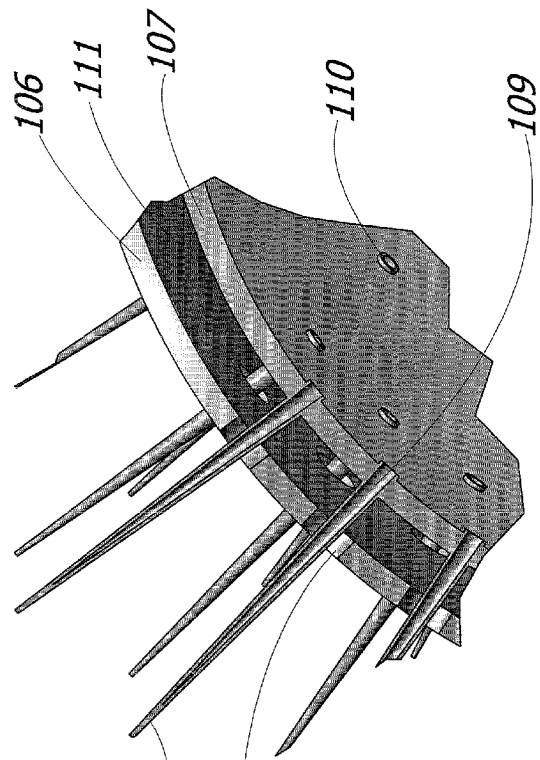
FIG. 13c is a magnified cross sectional view of the inner and outer membranes of the implantable cranium pump.

The implantable cranium pump unit 100 of the illustrated embodiment of the invention depicted in FIG. 10a comprises of two distinct polymer layers; an inner membrane 107 and the outer membrane 106 as best seen in FIG. 13c. Inner membrane 107 and outer membrane 106 are seamed together at the base and head of cranium pump 100 by a pump solenoid assembly 104 and a pump head assembly 103 respectively (FIG. 12). The pump solenoid assembly 104 and pump head assembly 103 provide a means for contracting and expanding the cranium pump 100 and are further discussed in more detail below. Both inner membrane 107 and outer membrane 106 are made from a skin-like polymer material. This material allows the pump 100 to be highly flexible during the drug delivery process and decreases the chances for infection or rejection from the body of a patient.

The space enclosed by inner membrane 107 is a medication reservoir 129 used for storing the drug Avastin or a mixture of medicating agents with Avastin as shown in FIG. 12.

Avastin is manufactured by Genetech Inc., a subsidiary of Roche Holding AG. Avastin is a monoclonal antibody to vascular endothelial factor (VEGF) and is currently approved by the FDA for recurrent malignant gliomas. Briefly, Avastin works on the premise that malignant tumors such as gliomas secrete VEGF, when then binds to the glioma endothelial cells. Avastin, by mopping up the VEGF, acts as an anti-angiogenesis agent. Typically Avastin is given intravenously every two weeks to a patient, however a variety of complications including poor wound healing, kidney damage, intracerebral hemorrhage, and venous thrombosis have been associated with such treatment. While Avastin has only been administered via intravenous means, promising new research suggests that direct intratumoral administration would be even more effective in treating tumors and less catastrophic for the patient. Such direct intratumor implementation would only be possible with the use of the above disclosed pump 100.

The size and volume of the medication reservoir 129 and thus the cranium pump 100 itself may be varied from patient to patient. A physician will make a determination of how much medication a particular patient will need and then the size of the medication reservoir 129 will be made accordingly. For example, a patient that needs large doses of medication will receive a cranium pump 100 with a larger medication reservoir 129 then a patient who only requires a small dose.

Figure 13A:
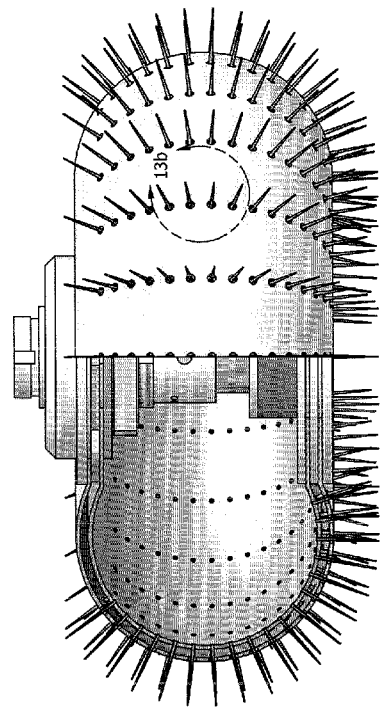
FIG. 13a is a partially cutaway cross sectional view of the implantable cranium pump with a polarity of injector spines highlighted.
Figure 13B:
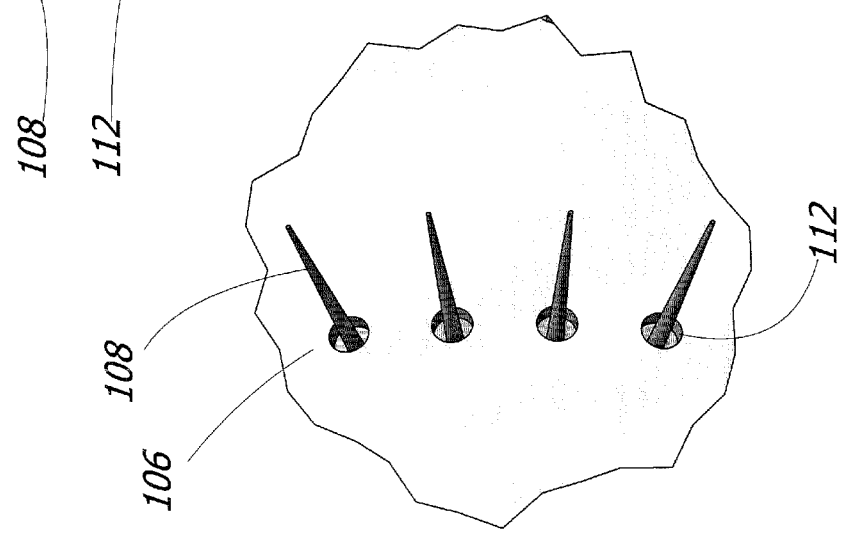

Turning again to FIGS. 13a-13c, the inner membrane 107 further comprises a plurality of small injector spines 108 distributed throughout the entire surface of the inner membrane 107. As can be seen in FIGS. 14a and 14b, the injector spines 108 may be comprised of hollow tubes 109 or a spiral design 133 with a pleated inlet 110 at its base where spine 108 meets the inner membrane 107 (FIG. 13c). The inner membrane 107 has a shape memory which effectively causes it to act as telescoping springs to rapidly extend and retract the injector spines 108 through the surface of the outer membrane 106. The injector spines 108 are also sufficiently long enough to penetrate the outer membrane 106 when the cranium pump 100 is in its most expanded state as shown in FIG. 10a. The injector spines 108 are tapered at their tips so that fluid flows substantially in only one direction, namely from the medication reservoir 129 to the surrounding tissue of the patient.

When the cranium pump 100 is being contracted or is in its supply stroke, the inner membrane 107 is pushed outward thus extending the injector spines 108 further past the outer membrane 106 and deeper into the patient's surrounding tissue. This process allows the pump 100 to deliver Avastin deeper into the affected tissue and thus the tumor itself in a more direct way than any prior art method. The injector spines 108 extend into the patient's tissue and the increased pressure created by the contracting cranium pump 100 pushes the Avastin out through the injector spines 108 at its most extreme extension point.

When the cranium pump 100 is expanding or is in its intake stroke, the inner membrane 107 collapses back to its original shape and thus retracts the injector spines 108 to their original position just outside of the outer membrane 106. When the injector spines 108 are retracted, the pressure differential of the cranium pump 100 will necessarily draw in a small amount of surrounding cerebral fluid into a sampling cavity 111. This is deemed beneficial however since the cerebral fluid will be eventually mixed with the Avastin and thus increasing the diffusion rate of the Avastin when it is pushed out of the injector spines 108 in any of the subsequent supply strokes. This process of extending and retracting the injector spines 108 is repeated for as long as the cranium pump 100 is activated.

Returning to FIG. 13c, the outer membrane 106 further comprises a plurality of micro pores 112 distributed throughout its entire surface. When the pump 100 is in the intake stroke, cerebral fluid is drawn into the pump 100 through the micro pores 112 due to the pressure differential that exists between the inside of pump 100 and the surrounding area outside of the pump 100. The amount of cerebral fluid that is drawn through the micro pores 112 is kept separated from the medication reservoir 129 by the inner membrane 107 and the lower portions of the injection spines 108. The volume of cerebral fluid that is then contained between the inner membrane 107 and outer membrane 106 then forms a sampling cavity 111. The components of cranium pump 100 is preferably composed of silicone, as this is the material currently used for ventriculoperitoneal shunts. However additional materials such as biodegradable material or other composites may be used without departing from the original spirit and scope of the invention.

Figures 15A, 15B:
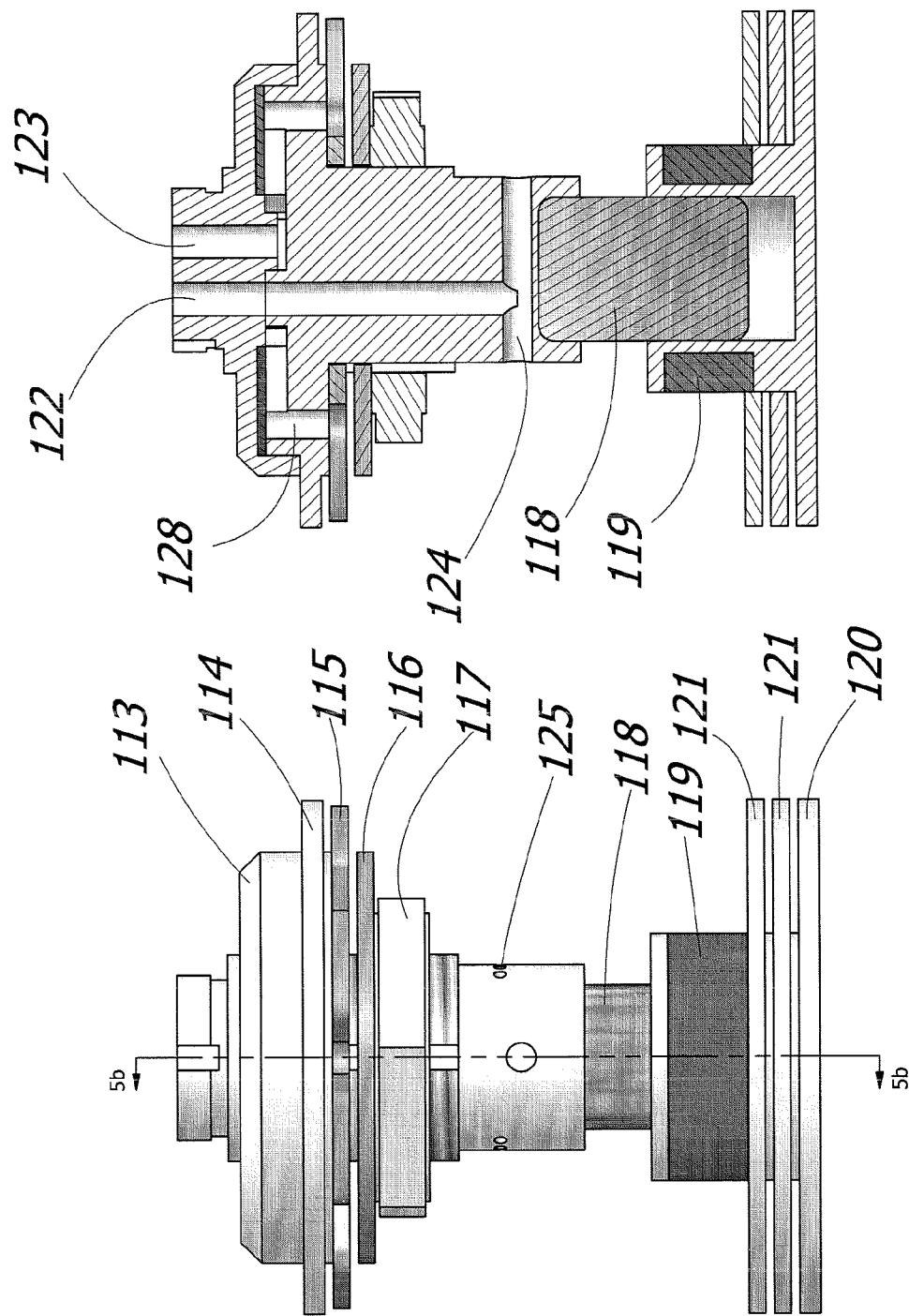
FIG. 15a is a front view of the pump actuator assembly.
FIG. 15b is a cross sectional view of the pump actuator assembly.

The detailed parts of the pump head 103 and pump solenoid 104 assemblies are shown in FIGS. 15a-16b. In FIG. 15a, the assembly is comprised of a coil 119 which can generate magnetic fields either reinforcing or opposing the magnetic field of a permanent magnet 118. The permanent magnet 118 is made of NbFe35 ceramic material however other materials may be used without departing from the original scope and spirit of the invention. The coil 119 may then be pulled or pushed away from the permanent magnet 118 depending on the current polarity of the coil 119. The coil 119 is coupled to a bobbin 120 and is constructed from a plurality of small (40 AWG) windings. The bobbin 120 is composed of several layers of bobbin washers 121. Because bobbin 120 is attached to the flexile skin-like material of the inner membrane 107, the coil 119 movement translates into an increase or decrease of pressure on the medication reservoir 129.

Controlling the amount of electrical current that passes through the coil 119 produces variable and regulated medication pressure which in turn adjusts the amount of Avastin passing through a plurality of injector spines 108 described above. Conversely, the controlled movement of the coil 119 acts as a pumping function serving to provide suction to the outer membrane 106 of the pump and thus draw in surrounding cerebral fluid from the patient.

The apparatus uses a method similar to respiration to not only pump drugs into the brain, but also to sample the immediate area by creating a negative pressure in the sampling cavity 111. As can be seen in FIG. 12, the pump solenoid 104 and pump head 103 use a magnet 118 and coil 119 as a solenoid to create attraction or repulsion between the pump head 103 and the bobbin 120. This motion is then translated to the cranium pump 100. The outer membrane 106 is made of a more ridged durra silicon rubber than the inner membrane 107. When the pressure is reversed by the pump solenoid 104, because the inner membrane 107 is softer than the outer membrane 106, the gap between the membranes increases and the negative pressure sucks in the cerebral fluids through the aspirator micro-pores 112 around the spines 108 on the outer membrane 106. Turning back to FIGS. 15a and 15b, this sample fluid then gets removed between a sampling washer 115 through sampling collection ducts 128 in a delivery/sampling head 114 and out through a connector plate 113.

The connector plate 113 has both a drug inlet 122 and a sampling tube 123 connection. The connector plate 113 also comprises all the electrical connections for the coil 119, the pressure sensor 131 (shown in FIG. 12) and the temperature sensors 132 (also shown in FIG. 12). The top of drug inlet 122 and the sampling tube 123 as well as various sensor and coil connections can be seen in FIG. 11b.

Figure 16A:
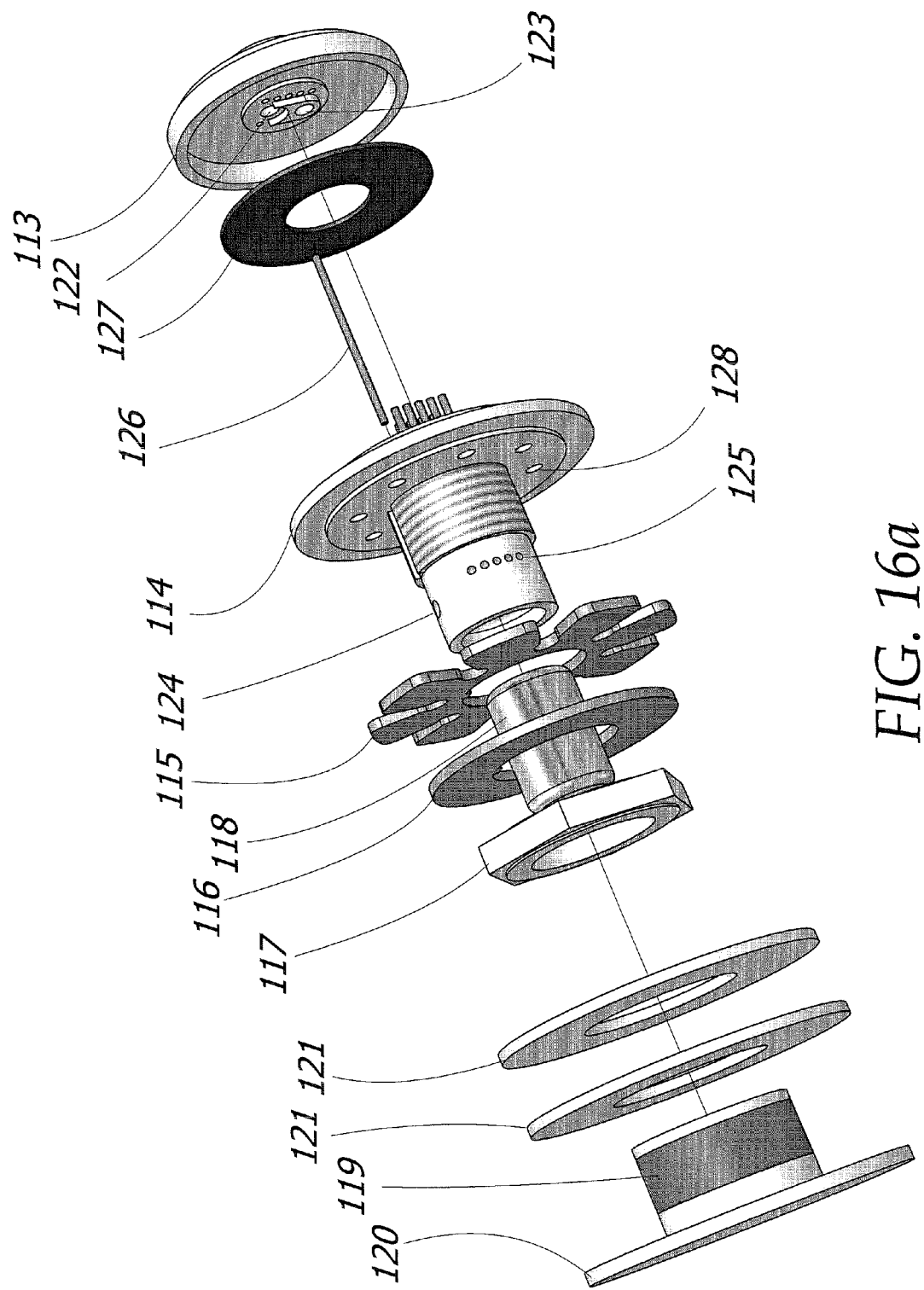
FIG. 16a is an exploded bottom view of the pump actuator assembly.
Figure 16B:
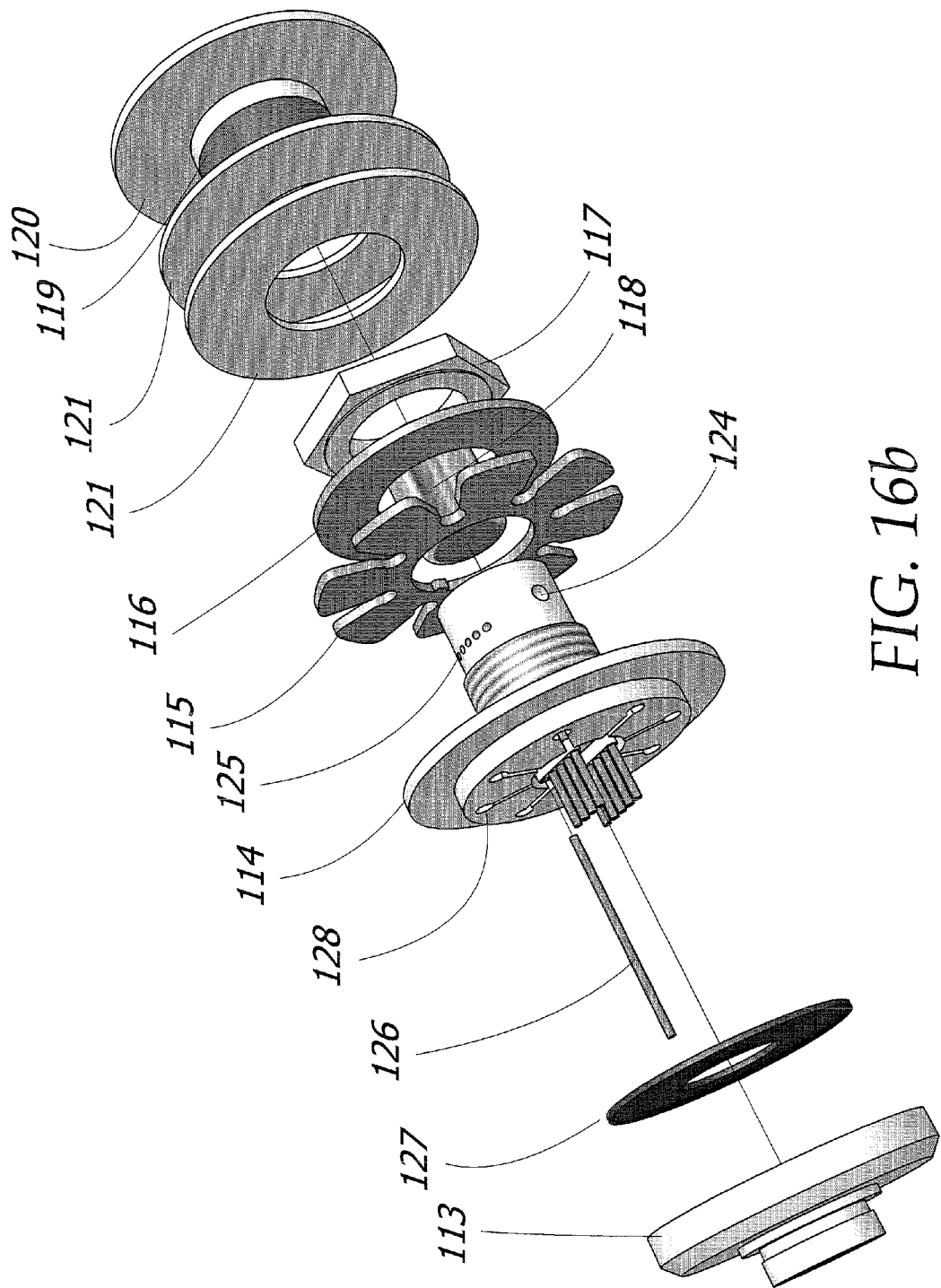
FIG. 16b is an exploded top view of the pump actuator assembly.

FIGS. 16a and 16b best show that the electrical connections are transferred through a series of sensor and coil pins 126 through the delivery/sampling head 114 to a plurality of sensor and coil connections 125 in the inner medication reservoir 129. Connections to the coil 119 are made with insulated flexible wire 130 (shown in FIG. 12).

Turning back to FIGS. 16a and 16b, the inner and outer membranes 107, 106 are attached and compressed by washers 121 to the bobbin 120. The bobbin 120 freely travels over the permanent NdFeB magnet 118. The magnet 118 is permanently coupled to the delivery/sampling head 114. The inner and outer membranes 107, 106 are also coupled directly to the delivery/sampling head 114. The sampling washer 115 and the bobbin 120 also provide the necessary gap of 0.020 inch for the medication reservoir 129. A compression nut 117 compresses an inner membrane washer 116 to clamp the inner membrane 107 against the delivery/sampling head 114. As seen in FIG. 15b, the delivery/sampling head 114 also comprises a drug dispersion tube 124 which releases the Avastin or mixture of medicating agents and Avastin to be administered to the patient into the medication reservoir 129.

Turning back to FIG. 10a, at the head of the cranium pump 100, the pump head assembly 103 located there is coupled to a seal connector 102 via a series of fluid lines and electronic connections enclosed in a pump-to-seal interconnect 101. The seal connector 102 is essentially a valve that controls the amount of fluid that is permitted to enter or leave the pump 100. When more Avastin is needed, the seal connector 102 opens and allows the Avastin to travel through the pump-to-seal interconnect 101 and enter the medication reservoir 129 below. When the correct amount of Avastin has been applied, the seal connector 102 closes and all incoming fluid flow stops. Additionally, the seal connector 102 houses a suction nozzle (not shown) that applies suction to the sampling cavity 111 and draws up recently acquired cerebral fluid up and out of the pump 100 and through the seal connector 102.

FIGS. 10b and 10c further depict the pump mode 145 and supply mode 144 as it is employed by the cranium pump 100. FIGS. 10b and 10c depict the electrostatic muscle 64 in its closed state 134 which is also the supply mode 144, where the Avastin or BRM are pumped out and transported from the cranium pump 100 to the desired tumor site or biological tissue of interest.

In FIG. 10b, the inlet nozzle is shown as 136, while an increasing chamber volume 141 is taking place. The increase in chamber volume causes flow 138 from the inlet 136 to enter the chamber 142 and at the same time, there is a small amount of fluid which flows from the outlet 137 into the chamber 142 as well. However, because of the venturi action of the inlet 136 and the outlet 137, the total net flow is from the cranium pump 100 into the chamber 142. In this case, the inlet 136 exhibits a diffuser action 143 and the outlet 137 exhibits a nozzle action 140.

FIG. 10c exhibits the electrostatic muscle 64 in its open state 135, which is also the pump mode 145. In this case there is a decrease in chamber volume 151, which causes a net flow to take place from the chamber 150 to the tumor site 41 through the outlet 148. Although there is a small amount of flow 147, from the chamber 150 to the inlet, the net flow is substantial and is from the chamber 150 to the tumor site 41. In this mode, the inlet 147 exhibits a nozzle action, 152 and the outlet exhibits a diffuser action 149.

Figure 1A:
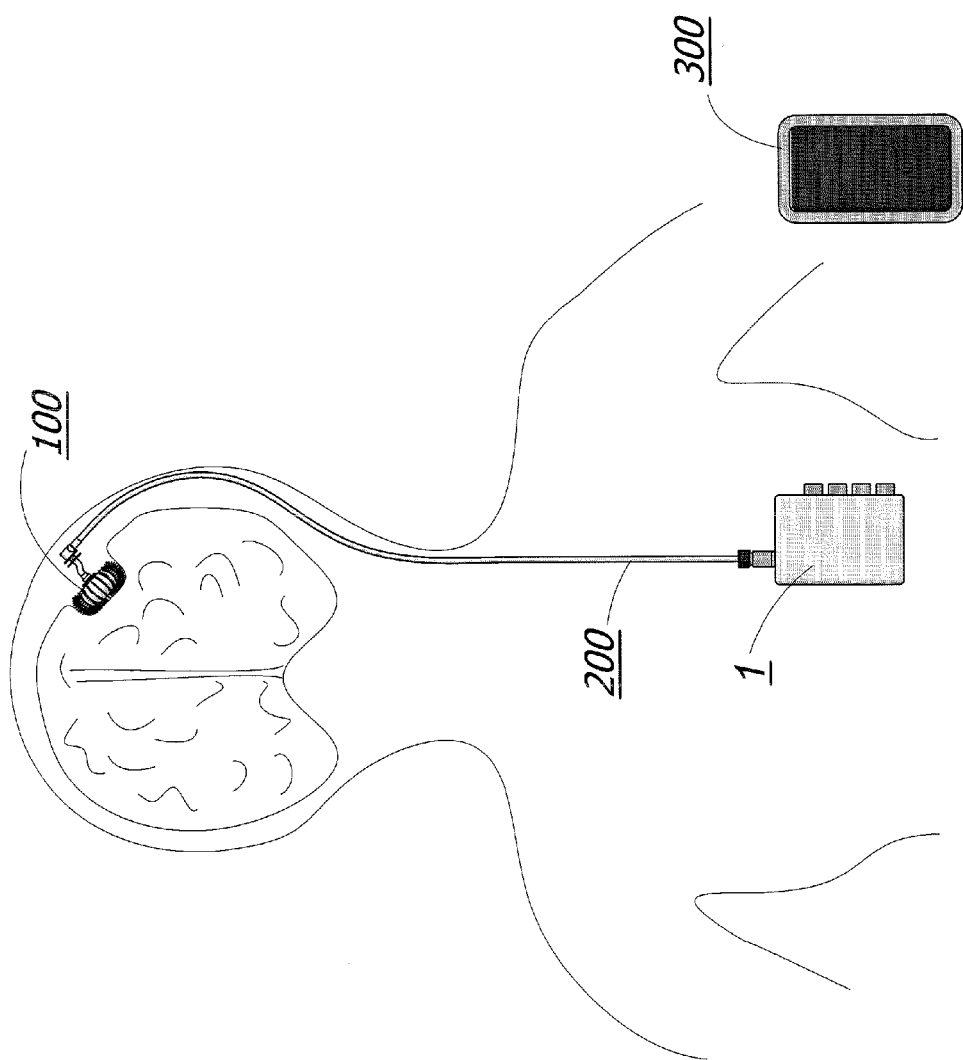
FIG. 1a is a diagrammatic cross sectional view of a patient's body after the implantable pump unit has been successfully implanted into the tumor cavity and placed under the patient's skull and dura and the CPD has been implanted beneath the skin in the chest cavity.

Turning to FIG. 1a, a delivery hose 200 is coupled to the seal connector 102 and a CPD 1 portion of the apparatus. The delivery hose 200 thus serves as a conduit between the pumping and analyzing portions of the current invention and houses a refill line, a return sample fluid line, and several electronics connections for various sensors and the coil 119.

After the cranium of the patient has been opened and the skull and dura have been successfully breeched, the tumor, or as much of the tumor as possible, is removed. The soft cranium pump 100 is then placed in the resulting cavity, and the skull cap is reattached. As can be clearly seen, the pump 100 is positioned on the patient's brain beneath both the dura and skull of the patient. The seal connector 102 is coupled to pump 100 and is firmly embedded within the dura of the patient with the top portion of the shunt protruding from the skull. The delivery hose 200 is coupled to the seal connector 102 and leads away from the pump 100 and down the back of the neck of the patient underneath the skin. The delivery hose 200 lies beneath the scalp of the patient for the entire distance between the seal connector 102 and the point where the catheter is connected to the analyzer 1 at the clavicular head. The purpose for maintaining the catheter 200 beneath the scalp is to give the patient a sense of normalcy and confidence while they are undergoing treatment.

Figure 1C:
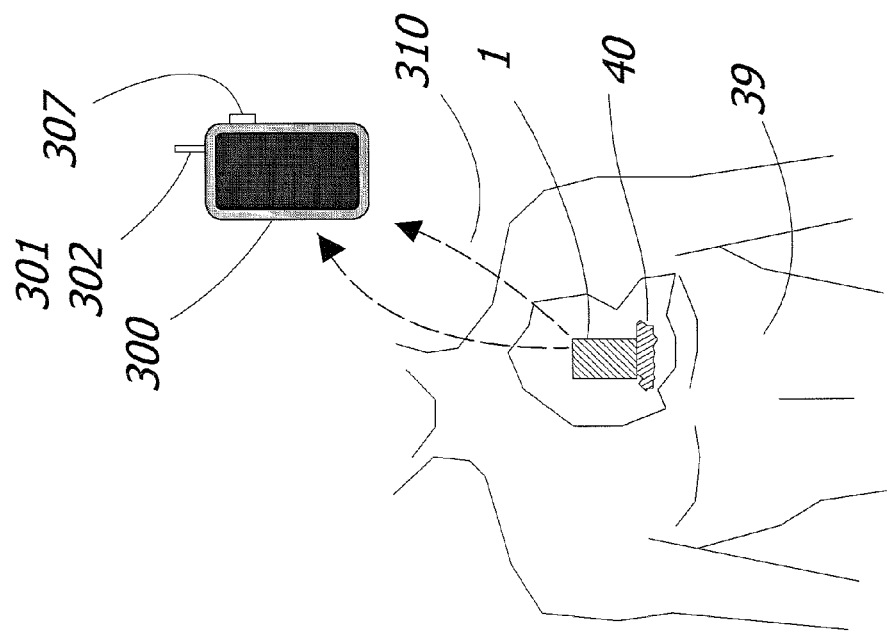
FIG. 1c is a diagram which illustrates the implantable pouch and its associated communications controller.
Figure 1B:
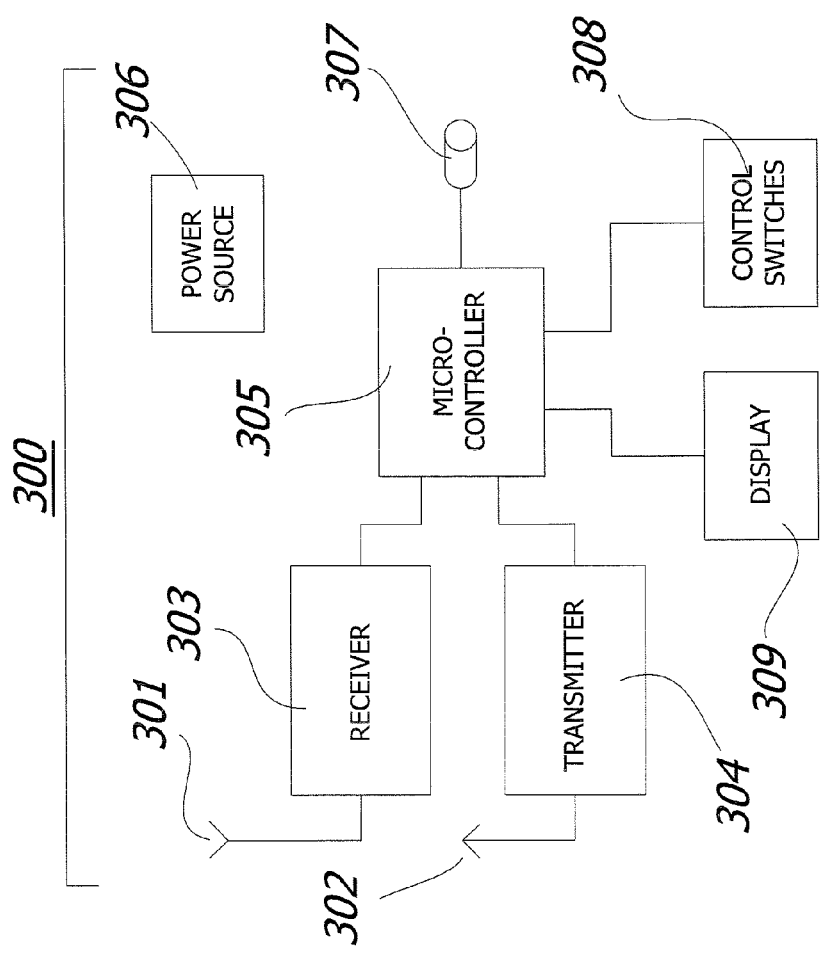
FIG. 1b is a block diagram of the architecture of the external control unit which communicates with the implanted apparatus.

FIG. 1b shows an external controller 300 which communicates with the chemotherapy pump device (CPD) 1. The CPD 1 communicates with the external controller 300 by the use of RF transmitter 304 and its associated antenna 302 and RF receiver 303 with its associated antenna 301. After implantation of the CPD 1 subcutaneously inside the patient 39, the system allows for programmability of the device in order to dispense the Avastin in proper intervals over time and in the prescribed doses. Once the CPD 1 and cranium pump 100 is implanted and is in operation, the clinician may decide to change the parameters of the operation such as the amount of medication dispensed onto the tumor site or the time intervals associated with the dispense process. The clinician communicates with the internal electronics of CPD 1 using an external controller 300 shown in FIG. 1b, which may be in the form of a desktop computer or any other similar appropriate device. The external controller 300 is able to communicate with the microcontroller in CPD 1 through its own microcontroller 305 via RF transmitter 304, its antenna 302, and the RF receiver 303 and its antenna 301, or via the serial communication port 307, located in the external controller 300. The new sets of commands are then transferred to the cranium pump 100. These new command data are then stored in the memory of the microcontroller of CPD 1, which is now programmed anew to perform the procedure as coded in the new instruction set.

In one embodiment, the external controller 300 is used to implement computer software that provides preoperative simulation of the infusion of Avastin and other intratumoral infusates to maximize infusion efficiency and minimize local toxicity to the adjacent brain from leakage of the infusate into the normal tissue by means of a diffusion model. The diffusion model is used to describe the drug dispersion with the brain's extracellular space due to both diffusion and convection. Specifically, brain geometry, drug properties, catheter dimensions and placement, and injection method are considered in this model. Other terms such as drug decomposition, chemical kinetic reaction, and bio-elimination can be incorporated to improve the accuracy of the prediction model.

In the first step, the patient-specific diffusion tensor imaging (a method of MRI) is used to construct a brain tumor model with accurate geometry (sharp boundaries and surfaces of the substructures). In the second step, the brain region is partitioned into small discrete volume grids. In the third step, a set of equations and boundary conditions describe flow physics and mass transfer between the finite volumes in the brain region. In the final step, the equations are solved numerically over the finite volume and the boundaries between the adjacent volumes.

The patient specific brain imaging data not only provides accurate size and shape of the tumor region but also permit reconstruction of physiologically consistent substructures and boundaries between regions in the brain. Brain and tumor tissue properties such as porosity, tortuosity, diffusivity, permeability, and hydraulic conductivity parameter's can be estimated from the brain location and reference literature. These parameters combined with the catheter placement and orientation respect to the tumor region allow estimation of location specific parameters such as diffusivity tensor, permeability tensor, and hydraulic conductivity tensor values required in the flow and mass transfer equations.

The brain including tumor region is partitioned into small triangular and quadrilateral elements using Delaunay triangulation. Each small finite volume is linked to its neighbors so as to form a logically connected computational mesh, which can be generated by grid generation software such as Fluent 2007. The grid sizes need to be large enough to minimize the number of volume elements for calculations yet small enough to be able to spatially resolve the anatomical properties of the tumor area. A typical simulation consists of approximately 20,000 to 30,000 volume elements distributed in the region covering about one quarter of the brain (300 cc). The flow and mass transfer equations are enforced over the computational domain consisting of these meshes.

The drug delivery to the brain is simply modeled as inserting aqueous solution consisting of drug solutes into porous brain tissues via an infusion catheter. The aqueous solution is assumed to be an incompressible Newtonian fluid whose motion can be described by the mass and momentum conservation equation. Additionally, the drug distribution is described by the species transport and chemical kinetics equations. The diffusion model consists of two parts: the flow inside the catheter and the flow in porous brain tissues.

For the flow inside the catheter, the model divides the space inside the lumen of the catheter into small finite elements. The fluid flow between the finite elements is modeled with the continuity and Navier-Stokes equations as shown in Equations 1 and 2, respectively. The continuity equation (Eq 1) describes that the fluid is incompressible.

$$\vec{\nabla} \cdot (\rho \vec{v}_f) = 0 \qquad (1)$$

The Navier-Stokes equation (Eq 2) describes that the momentum of the fluid flow is conserved. It states that any change in fluid velocity in the catheter (the left-hand side of the equation) is due to the pressure gradient (caused by the pumps) and resistance of the flow due to fluid viscosity.

$$\rho\left(\frac{\partial \vec{v}_f}{\partial t} + \vec{v}_f \cdot \vec{\nabla} \vec{v}_f\right) = -\vec{\nabla} p + \mu \vec{\nabla}^2 \vec{v}_f \quad (2)$$

The movement of the drug molecules inside the catheter due to the flow can be modeled with the species transport equation as shown in Equation 3. It states that the change in concentration of the molecules due to diffusion and convection (the left-hand side of the equation) depends on the divergent of the product of the diffusivity and concentration gradient of the molecules in the fluid.

$$\frac{\partial C_f}{\partial t} + \vec{v}_f \cdot \vec{\nabla} C_f = \vec{\nabla} \cdot (D_b \vec{\nabla} C_f) \quad (3)$$

The flow inside the brain is modeled as the fluid flow in a porous medium. The brain is partitioned into small finite elements and the flow between these elements is modeled with the continuity equation and Darcy's Law as shown in Equations 4 and 5, respectively. The continuity equation (Eq 4) describes that the loss of fluid in the flow is due to the absorption into the porous medium. The fluid velocity in tissue is related to average fluid velocity through porous tissue, $\vec{v}_t = \epsilon \vec{v}_p$, through the porosity. At the tip of the catheter, the average fluid velocity is the same as the fluid velocity coming out of the catheter: $\vec{v}_p = \vec{v}_f$. The amount of fluid loss captured in the sink term is a function of the difference between the interstitial fluid pressure and the venous pressure: $S_B = f(p - p_v)$.

$$\vec{\nabla} \cdot (\rho \vec{v}_t) = S_B \quad (4)$$

The fluid dynamics in the porous brain is embodied in the Darcy's Law (Eq 5), which states that the momentum of the fluid flow is conserved. It states that any change in fluid velocity in the brain (the left-hand side of the equation) is due to the pressure gradient (caused by the flow out of the catheter) and resistance of the medium to the flow.

$$\frac{\rho}{\varepsilon}\left(\frac{\partial \vec{v}_t}{\partial t} + \varepsilon^{-1}(\vec{v}_t \cdot \vec{\nabla})\vec{v}_t\right) = -\vec{\nabla} p - \Re^{-1} \vec{v}_t \quad (5)$$

The movement of the drug molecules inside the brain due to the flow described in Eq 5 can be modeled with the species transport equation as shown in Equation 6. It states that the change in concentration of the molecules due to diffusion and convection (the left-hand side of the equation) depends on the divergent of the product of the diffusivity tensor of the brain medium and concentration gradient of the molecules in the fluid. The accuracy of the model can be improved by incorporating the loss of drug molecules due to decomposition and bio-elimination.

$$\varepsilon \frac{\partial C_t}{\partial t} + \vec{v}_t \cdot \vec{\nabla} C_t = \vec{\nabla} \cdot (\mathcal{D}_e \vec{\nabla} C_t) + R(C_t, \vec{x}) + S(C_t, \vec{x}) \quad (6)$$

The completeness of the diffusion model is captured in the boundary condition assumptions listed below. At the catheter inlet, the infusion flow rate or pressure and concentration of drug are assumed to be constant. At the interior wall inside the lumen of the catheter, the flow is assumed no slip, $$\frac{\partial p}{\partial n} = 0,$$

and the drug doesn't penetrate (zero flux) into the catheter wall, $\vec{n} \cdot \vec{\nabla} C_f = 0$ and $\vec{v}_f = 0$. At the outer surface of the catheter, the same boundary conditions are assumed as in the inside. At the catheter tip, the continuity of flow is assumed: $\vec{v}_f|_{lumen} = \vec{v}_{Cout} = \vec{v}_t$, and, $p_{lumen} = p_{Cout}$, and $C_f|_{lumen} = C_f$. At the lateral ventricles or capillary surfaces, the fluid pressure is the same as the pressure of the Cerebrospinal fluid (CSF). No fluid flow through the ventricle and capillary walls, $\vec{n} \cdot \vec{\nabla} v_x = 0$, $\vec{n} \cdot \vec{\nabla} v_y = 0$. Only the mass transfer through the permeable ventricle and capillary walls is assumed: $-D_e(\vec{n} \cdot \vec{\nabla} C_t) = k(C_t - C_\infty)$. Molecule transfer through permeable boundary is only one way; drug molecules can leave but cannot return. Bio-elimination "sink term" is assumed as a function of the difference between interstitial pressure and venous pressure: $S_B = f(p - p_v)$.

The six partial differential equations (Eq 1-6) are applied to the discrete volumes in the model to produce a set of non-linear algebraic equations for the entire brain model. These equations are solved with proper boundary condition using the iterative Newton-Krylov method and simulated using commercial fluid dynamics software such as Fluent.

The microcontroller located in CPD 1 and implanted inside the patient's body 39 communicates with the external controller 300 via RF transmitter 304 and RF receiver 303 thereby sending its collected data to the external controller 300. This feature enables the clinician to collect data and to determine the state of the patient throughout the period of treatment. These data are stored inside the external controller 300 providing chart history of the treatment status of the parameters associated with the tumor site. The CPD 1 transmits data for collection and storage. The external controller 300 is controlled by the user via the settings in control 308 and it also displays the amount of Avastin dispensed over time by the cranium pump 100 on its display 309. Data collected in this manner can be used to correlate behavior pattern of a particular patient and his or her chart history. One can write a data collection and analysis program which can be displayed by the external controller 300. Once the data are collected from the CPD 1, the external controller 300 or the host PC can then plot the data on a time scale and analyze the data further. It is significantly better to correlate between the input and the output or between cause and effect to mirror the action of the cranium pump 100 and its host tumor site. Such data in the form of historical plot of cause and effect benefit the patient 39 and aide in future research. The entire unit as shown in the figure is run by power obtained from its power source 306.

FIG. 1c is an illustration of a patient 39 with tumor of the form glioma with the implanted pump 100. The external controller 300 with its associated serial port 307 and receiver and transmitter antennae 303 and 304 respectively is shown in its bidirectional communication model with the implanted CPD 1 via the RF path 310.

Turning to FIG. 4a, the CPD 1 comprises a delivery connector 7 where the delivery hose 200 couples with the CPD 1. The delivery connector 7 contains a drug outlet 4, a sample return 5, and a plurality of sensor connections 6 for controlling the pump unit 100 and for analyzing the sample fluid that is obtained from the cranium of the patient. The drug outlet 4 is the aperture in which Avastin or mixtures of medicating agents with Avastin are sent from the CPD 1 through the delivery hose 200. Similarly, the sample return 5 is the aperture where cerebral fluid that has been collected by pump 100 is returned by the delivery hose 200 and enters the CPD 1 for analysis. The process by which the external CPD 1 sends Avastin or medicating agents mixed with Avastin and receives sample fluid obtained from the patient through the delivery hose 200 is explained in further detail below.

Figure 2:
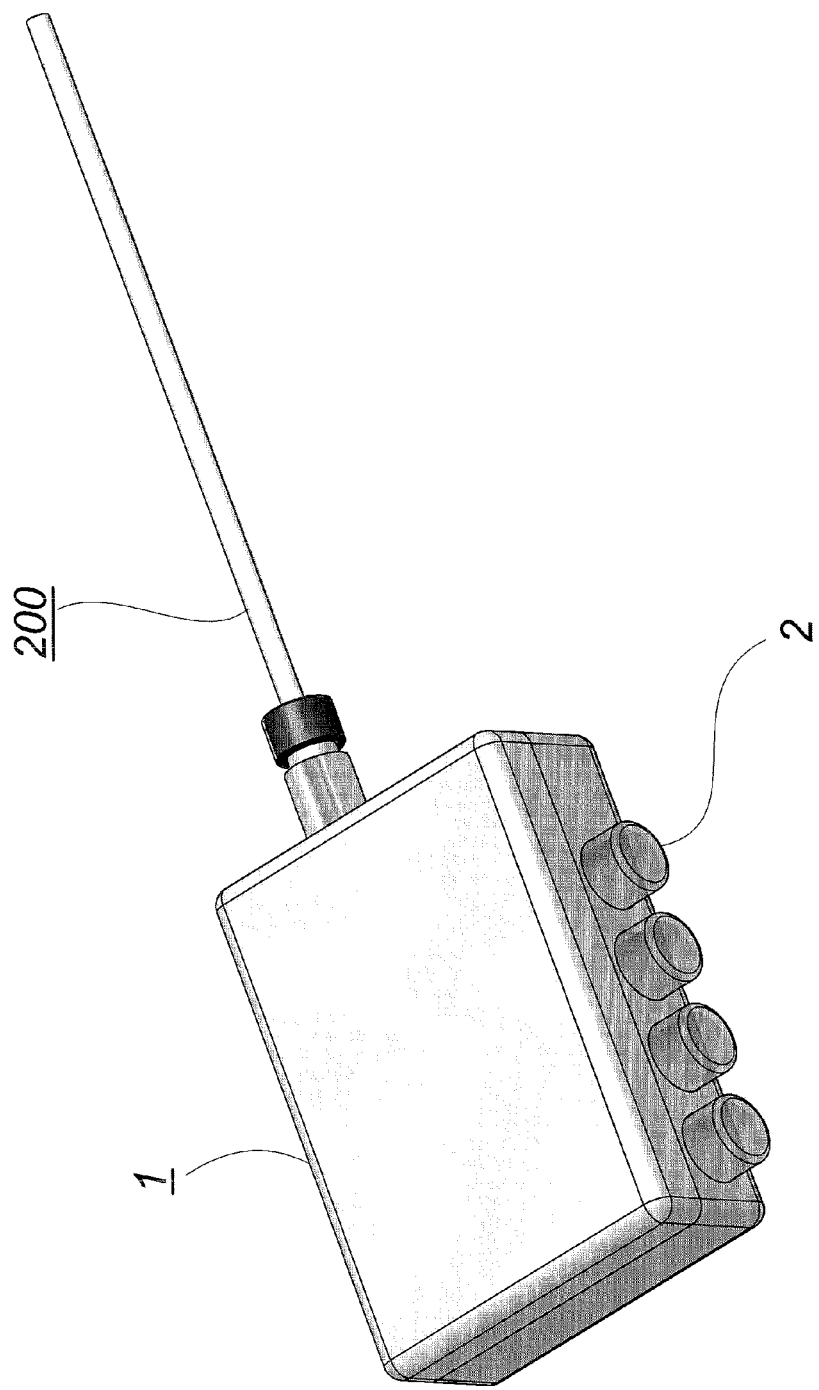
FIG. 2 is an isometric view of the CPD.
Figure 3C:
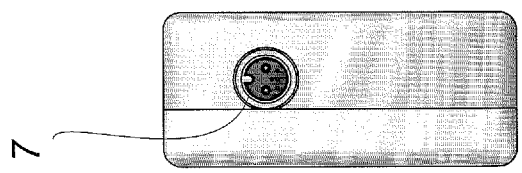
FIG. 3c is a right side view of the CPD.
Figure 3A:
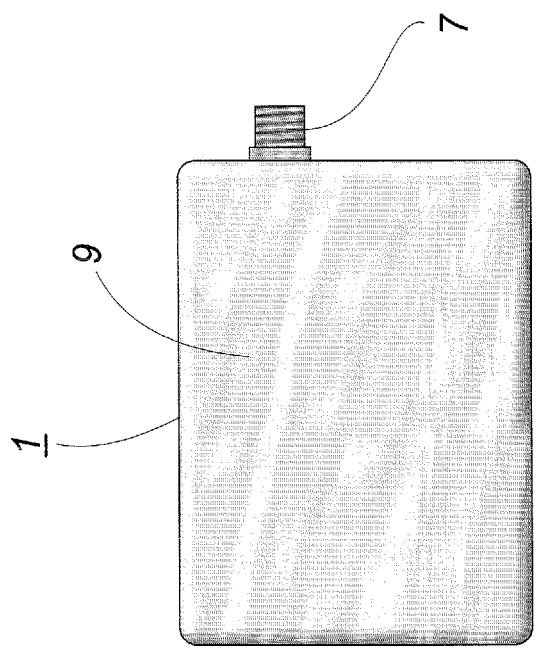
FIG. 3a is a front view of the CPD.
Figure 3D:
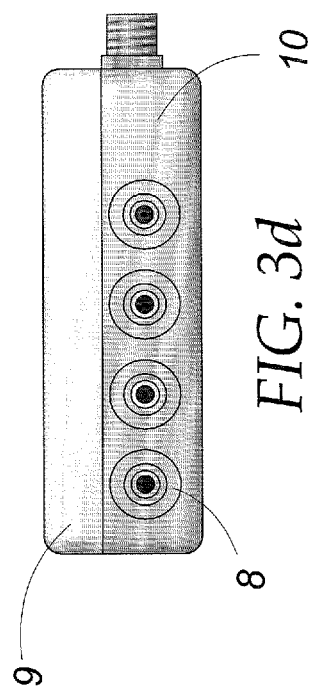
FIG. 3d is a bottom view of the CPD.
Figure 3B:
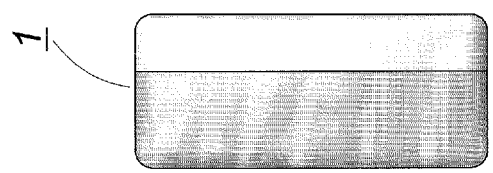
FIG. 3b is a left side view of the CPD.

Up to four drug ampoules 2 (FIG. 2) can be deposed on the bottom portion 10 of the external CPD 1 in four separate ampoule bays 8 as depicted in FIG. 3d. It is to be expressly understood that fewer or additional ampoule bays may be present without departing from the original spirit and scope of the invention. To introduce Avastin into the CPD 1, a drug ampoule 2 is inserted into the ampoule bay 8. Drug needles 18 extending from the interior of the CPD 1 shown in FIG. 7a penetrate the ampoules 2 and carry the Avastin. The CPD 1 then draws in the Avastin in a series of steps that are described below.

Figure 6:
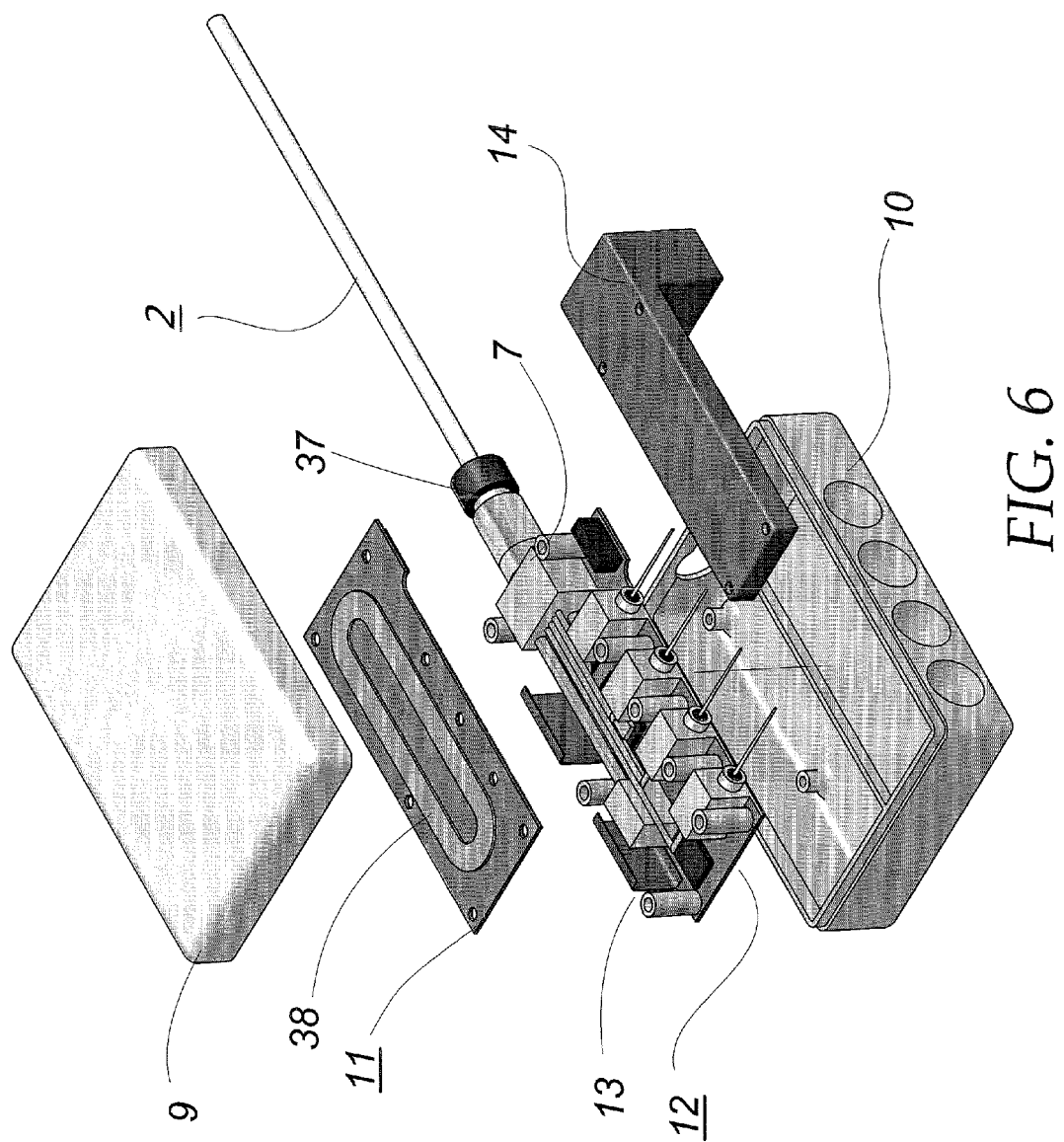
FIG. 6 is a fully exploded view of the CPD.

Turning to FIG. 6, the interior of the CPD 1 is comprised of two assemblies; a pump electronics assembly 12 and an induction charger assembly 11. The pump electronics assembly 12 and the induction charger assembly 11 are both housed within the external CPD 1 and are joined by an electronics interconnect cable 13 as best seen in FIGS. 7a and 7b.

The pump electronics assembly 12 is shown in greater detail in FIGS. 8a and 8b. As seen in FIG. 8b, the pump electronics assembly 12 contains a drug delivery CPU 27 that stores its program and data into two FLASH memories 28. Pre-stored information such as look-up tables and the like are stored on the FLASH memories 28. The drug delivery CPU 27 runs a pre-installed intelligent chemo delivery software program and controls an ampoule pump integrated circuit 20, a return pump integrated circuit 19, and a delivery valve drift integrated circuit 22 as seen in FIG. 8a. The drug delivery CPU 27 also communicates with a lab-on-a-chip 21 and receives important treatment data such as sample temperature data through the sensor inputs 6 in the delivery connector 7 seen best in FIG. 6.

The drug delivery CPU 27 is pre-programmed and is capable of transmitting data through a Bluetooth® transceiver 29. The Bluetooth transceiver 29 is connected to a Bluetooth® antenna 30. A user or qualified physician who wishes to change the patient's drug regimen from a remote location first sends the data to the patient. The sent information is then picked up by the Bluetooth® transceiver 29 and antenna 30 and is then stored on the FLASH memory chips 28. When the drug delivery CPU 27 retrieves information from the FLASH memory chips 28 it adjusts the drug regimen (dose, scheduling, etc.) according to the user's data instructions.

Figure 5:
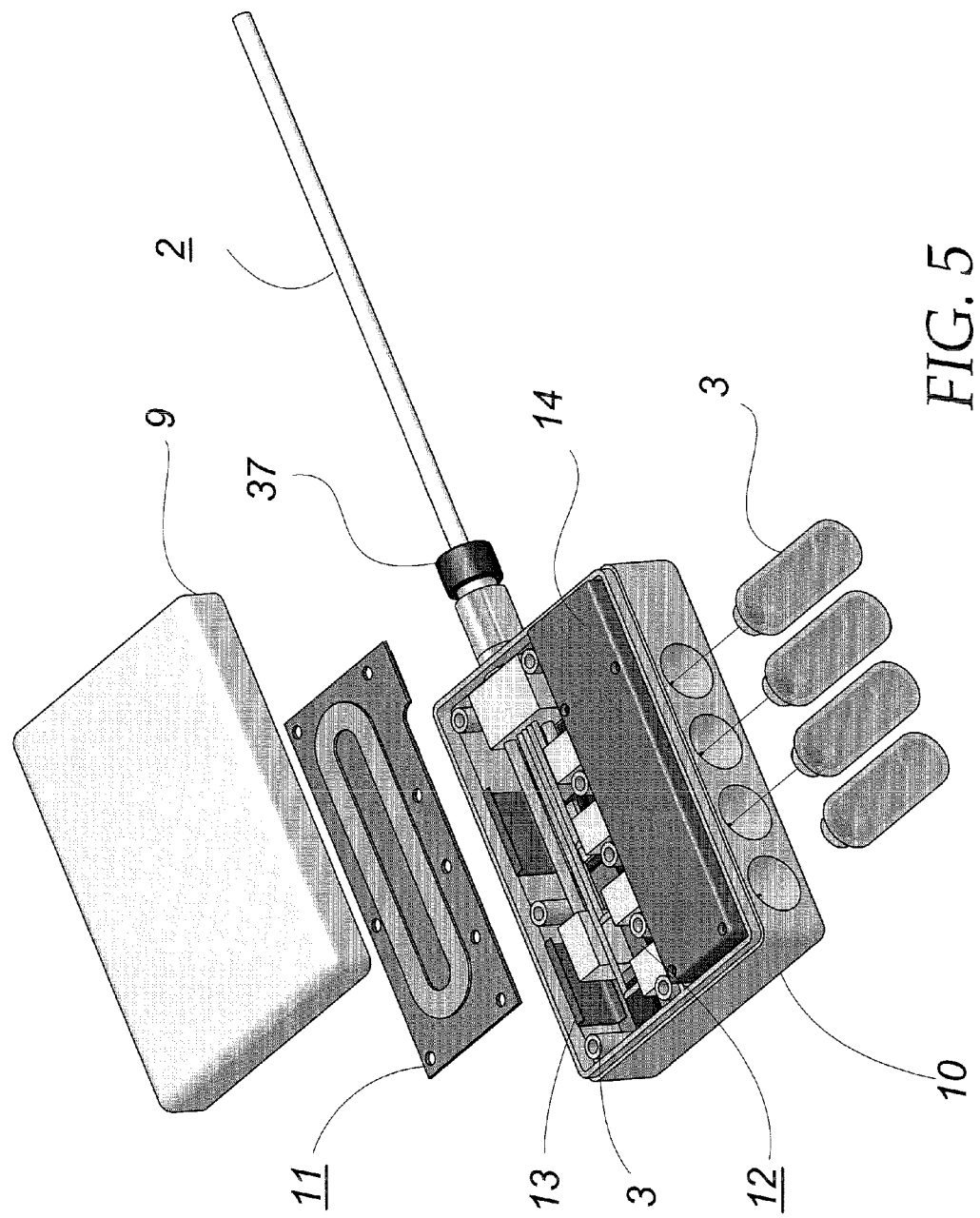
FIG. 5 is a partially exploded view of the CPD.

The external CPD 1 is capable of delivering up to four different drugs simultaneously with high accuracy in the following manner: The pump electronics assembly 12 of FIG. 8a comprises up to four piezoelectric pumps 17 driven by a corresponding ampoule pump integrated circuit 20 that together pump the Avastin out of the ampoule 2. The use and manufacture of piezo pumps are well known to those in the art. Fewer or additional piezo pumps 17 than what is depicted in FIG. 8a may be used without departing from the original spirit and scope of the invention. The pump needles 18 are sufficiently long enough so that when a drug ampoule 2 is attached to the piezo pump 17 as depicted in FIG. 2, the Avastin at the bottom of the ampoule may be accessed. Pump needles 18 coupled to the piezoelectric pumps 17 penetrate the ampoules 2 and the piezoelectric pump 17 pumps the Avastin through a drug manifold tube 24 and into a delivery valve 15 and out through the drug delivery connector 7. The delivery valve 15 is regulated by a delivery valve driver integrated circuit 22 which is controlled by the drug delivery CPU 27. The Avastin, after being pumped through the delivery connector 7, then enters into the delivery hose connector 37 (FIG. 5) via the drug output 4 on the delivery connector 7 depicted in FIG. 4b. The Avastin is then pumped through the delivery hose 200 and into the cranial pump unit 100 via the seal connector 102. In FIG. 5, the delivery hose 200 couples to the CPD 1 via a delivery hose connector 37.

The external CPD 1 is fully programmable and runs intelligent software to determine what and how much drug is required. The regulation loop of the intelligent drug delivery system uses a return sample of fluids from the "delivery area" to determine the necessary response. In FIG. 5, the return sample fluid obtained from the patient travels through the delivery hose 200, through the delivery hose connector 37, and then enters delivery connector 7 through the sample return 5 as shown in FIG. 4b. Turning to FIG. 8a, after the sample fluid passes from the delivery connector 7, the sample fluid enters the delivery valve 15. The negative pressure necessary to pump the sample is created by the return piezoelectric pump 16 that is powered by a return pump driver integrated circuit 19. The fluid sample then travels from the delivery valve 15 into a return pump input tube 25 and into a lab-on-a-chip 21 that senses the chemical composition of the sample. The return piezoelectric pump 16 continues pumping the sample fluid through itself and back out into a return output pump tube 23. The sample fluid is then mixed together with the delivery drug in the delivery valve 15, to continue a closed loop cycle to be returned to the collection site.

The second main assembly, the induction charger assembly 11, is depicted in greater detail in FIGS. 9a and 9b. The induction charger assembly 11 provides with a means for charging a lithium ion battery 14 (shown in FIG. 5). An induction coil 38 coupled to the induction charger electronics assembly 11 receives a high frequency (50 Khz) induced magnetic field from a similar charging coil from an external battery charger device (not shown). The induction coil 38 is coupled to a rectifier 35 shown in FIG. 9b. The rectifier 35 converts the high frequency voltage to a DC voltage that is filtered by an inductor 34 and capacitors 33. A battery charger controller 32 regulates the charging of the battery 14. The charger connector 36 is both for powering the electronics as well as charging the lithium ion battery 14. The battery 14 is appropriately sized to provide sufficient power for days of service without the need of charging.

The lithium ion battery 14 preferably has an "L" shape as shown in FIG. 6 so as to leave sufficient space available for the pump needles 18 and drug ampoules 2 within the housing of the CPD 1 and is sized to provide sufficient power for days of service without the need of re-charging. However it is to be expressly understood that other varieties of batteries with various life spans and shapes may also be used without departing from the original scope and spirit of the invention. The lithium ion battery 14 is coupled directly to the housing of the CPD 1 and is removable so that when the stored energy has been depleted from the battery 14, it may be easily replaced.

Filling the ampoules 2 with Avastin and having the Avastin then delivered intratumor by the pump 100 and its injector spines 108, eliminates the blood brain barrier as a potential obstacle. As discussed above Avastin is an antibody and thus would normally have a difficult time getting to the glioma cells directly without the pump 100 penetrating the brain blood barrier. Delivering the Avastin directly into the tumor also allows for more concentrated doses which eliminates the side effects associated with the systemic intravenous delivery of Avastin listed above, including intracerebral hemorrhages which can be catastrophic to the patient. Finally, the lab-on-a-chip 21 comprises means for directly monitoring the VEGF levels in the tumor. Avastin, as disclosed above, lowers the levels of VEGF in the tumor. Thus when the lab-on-a-chip 21 gives a current VEGF level, it is also therefore simultaneously giving a direct measurement and assessment of the effectiveness of the intratumor administration of the Avastin.

In patients in whom a resection cannot be performed, an alternative embodiment of the current invention involving a multidelivery catheter 200 is employed. A method for delivering intratumoral Avastin into the tumor in a patient comprises surgically implanting a multidelivery catheter 200 beneath the skull and dura of the patient into a treatment site. The multidelivery catheter 200 is then coupled to an external analyzer unit 300. The external analyzer unit 300 is the same external analyzer unit 300 described above with regard to the previous embodiment. The multidelivery catheter 200 is then operated within the treatment site of the patient in order to infuse the intratumoral Avastin to the treatment site. The multidelivery catheter 200 is then used to suction in a sample of cerebral fluid from the treatment site and transfer it to the external analyzer unit 300. In the same manner as described above with regard to the previous embodiment, the external analyzer unit 300 is then used to track and monitor the progress of the patient's treatment via the external analyzer unit 300. Additionally in the same manner as described above with the previous embodiment, the external analyzer unit 300 comprises the means for altering and changing the patient's treatment. Finally, a reservoir of intratumoral Avastin that is located within the external analyzer unit 300 may be refilled and replenished as needed.

Also as similarly described above, the external analyzer unit 300 comprises means for displaying the amount of intratumoral Avastin dispensed over time by the multidelivery catheter 200 within the treatment site.

In one particular embodiment, the suctioning in of the sample cerebral fluid from the treatment site comprises suctioning in the sample cerebral fluid in at least two proximal ports (not shown) defined in the proximal end of the multidelivery catheter 200. The means for tracking and monitoring the progress of the patient's treatment by the external analyzer unit 300 further comprises passing the sample cerebral fluid through a means for spinal fluid analysis in the external analyzer unit 300. The sample of cerebral fluid passes through a means of analysis on the external analyzer unit 300 that comprises means for measuring the effectiveness of the administration of the intratumoral Avastin.

In another embodiment, the method step of measuring the effectiveness of the intrtumoral Avastin administration further comprises displaying the results obtained from the means of the analyzer unit on a display.

In an alternative embodiment, the external analyzer unit 300 further comprises means for providing a preoperative simulation of the infusion of the intratumoral Avastin and other intratumoral infusates to maximize efficiency and minimize toxicity by means of a diffusion model.

The external analyzer unit 300 further comprises entering command functions and data into the external analyzer unit 300 from a remote keypad (not shown) and displaying the commands on a display 309. The entering of command functions may comprise sending command functions and data to the external analyzer unit 300 by means of a Bluetooth® transceiver and antenna.

The refilling and replacing of the reservoir of intratumoral Avastin located in the analyzer unit also comprises refilling and replacing at least four drug ampoules coupled to the analyzer unit, wherein at least one of the four drug ampoules is for Avastin.

Figure 17:
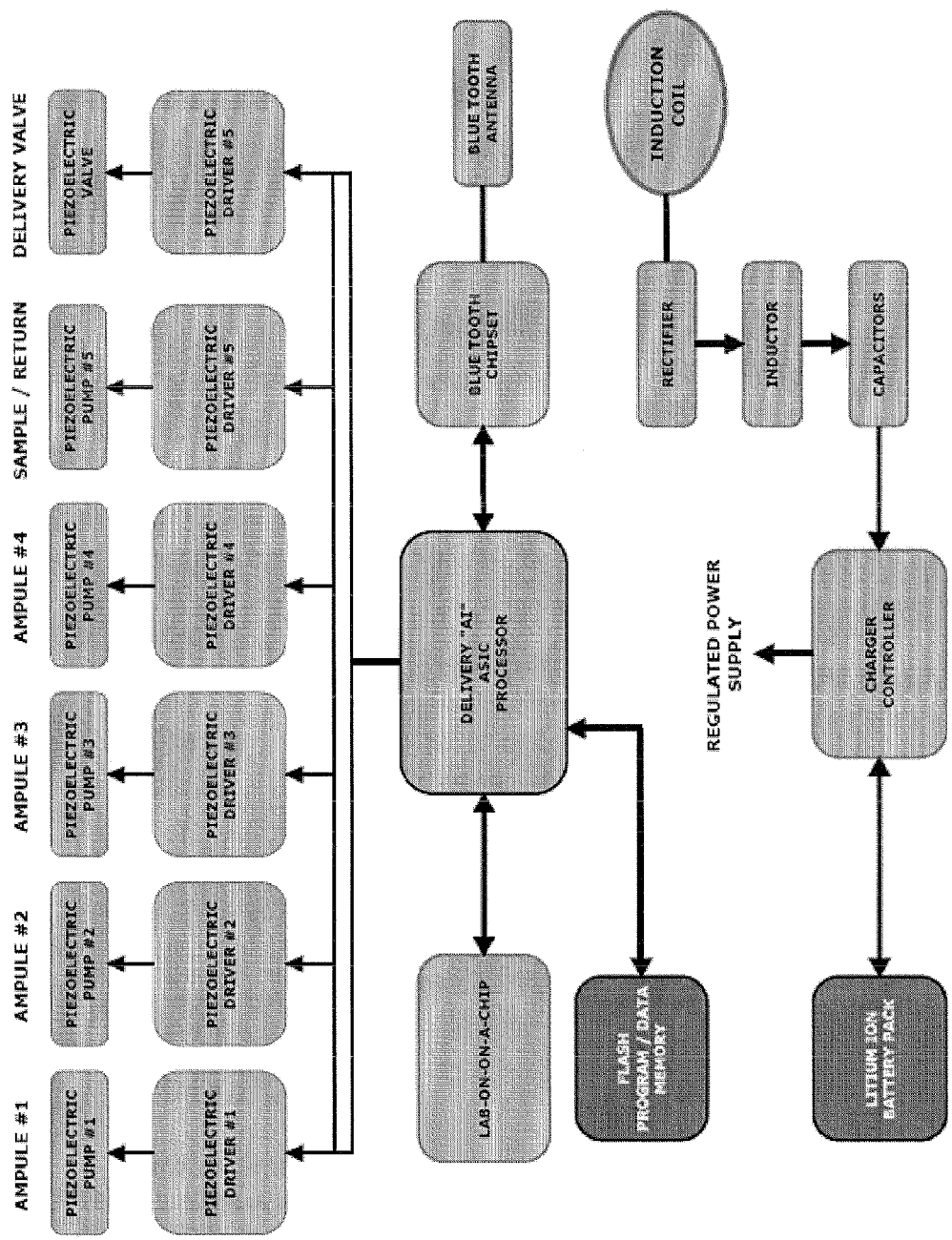
FIG. 17 is a functional block diagram of the pump actuator assembly.
Figure 18:
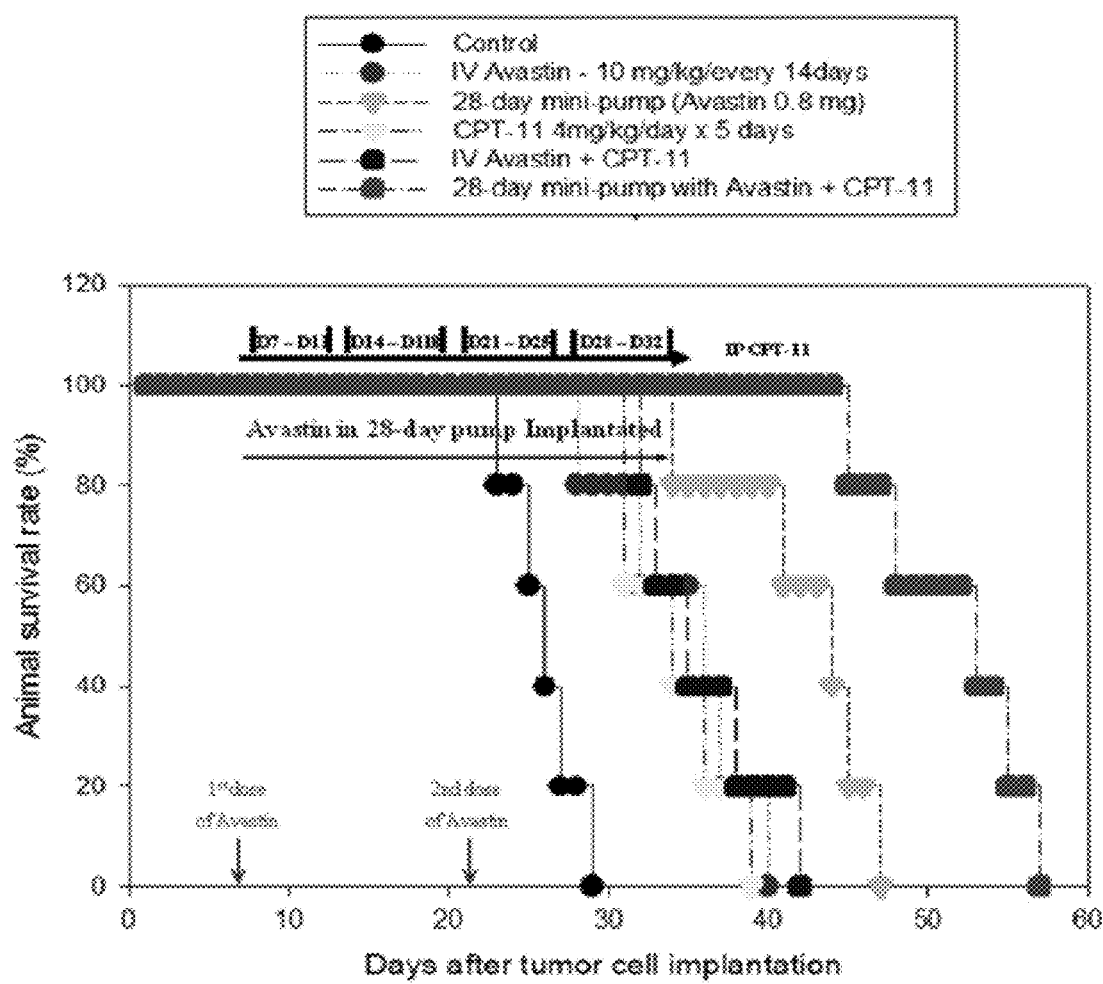
FIG. 18 is a graph of the results of a study conducted using mice implanted with glioma cells and treated with chemotherapeutic agents (including intratumoral Avastin) both systemically and via an implanted cranium pump, demonstrating superior survival in mice treated with intratumoral Avastin or intratumoral Avastin and CPT-11, compared to intravenous Avastin with or without CPT-11

FIG. 17 is a functional circuit diagram further illustrating the relationship between the elements of CPD 1 described above.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

For example, one skilled in the art may produce a device with fewer or additional drug ampoule bays or piezoelectric pumps without departing from the original scope and spirit of the invention.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

The invention claimed is:

1. A method for delivering Avastin into a brain tumor in a patient comprising:
    surgically implanting a cranium pump beneath the skull and dura of the patient's brain into a treatment site;
    coupling the cranium pump to an analyzer unit via a fluid exchange catheter;
    operating the cranium pump within the brain of the patient in order to infuse Avastin to the treatment site under control of the analyzer unit;
    suctioning in a sample of cerebral fluid from the treatment site and transferring it to the analyzer unit;
    tracking and monitoring the progress of the patient's treatment via the analyzer unit;
    altering and changing the patient's treatment proactively by controlling the analyzer unit via an external controller communicated to the analyzer unit by an RF link, the external controller allowing proactive alteration of a delivery schedule of Avastin to the brain of the patient by the cranium delivery pump based on measurements of a plurality of tumor parameters obtained from the cranium delivery pump and quantified by the analyzer unit;
    displaying the tumor parameter measurements on a display coupled to the external controller; and
    refilling and replacing a reservoir of Avastin located in the analyzer unit,
    wherein suctioning the sample of the patient's cerebral fluid further comprises suctioning the sample cerebral fluid at a variable rate into an intra-membrane reservoir defined between an outer and inner membrane in the cranium pump by the oscillation of a magnetic solenoid and a plurality of pores defined within the surface of the outer membrane and around each distal tip of a plurality of hollow needles coupled to the inner membrane.

2. The method of claim 1 where operating the cranium pump comprises:
    contracting and expanding a plurality of hollow needles fluidly coupled to an inner membrane reservoir in the cranium pump by oscillation of a magnetic solenoid;
    extending the plurality of hollow needles through an outer membrane and an intra-membrane reservoir defined between the outer membrane and inner membrane reservoir when the inner membrane reservoir is being expanded;
    retracting the plurality of hollow needles through the outer membrane and the intra-membrane reservoir defined between the outer membrane and the inner membrane reservoir when the inner-membrane reservoir is being contracted such that the distal ends of the plurality of hollow needles do not retract past the outer membrane; and
    preventing any fluid communication between the inner membrane reservoir and the intra-membrane reservoir.

3. The method of claim 1 where tracking and monitoring the progress of the patient's treatment further comprises passing the sample of cerebral fluid through a lab-on-a-chip in the analyzer unit.

4. The method of claim 3 where passing the sample of cerebral fluid through a lab-on-a-chip further comprises measuring the effectiveness of intratumoral Avastin administration with the lab-on-a-chip.

5. The method of claim 4 where measuring the effectiveness of intratumoral Avastin administration further comprises displaying the results obtained from the lab-on-a-chip on a display.

6. The method of claim 1 further comprising providing a preoperative simulation of the infusion of Avastin and other intratumoral infusates to maximize efficiency and minimize toxicity by means of a diffusion model.

7. The method of claim 1 where altering and changing the patient's treatment by controlling the analyzer unit further comprises entering command functions and data into the analyzer unit from a remote keypad and displaying the commands on a display.

8. The method of claim 7 where altering and changing the patient's treatment by controlling the analyzer unit further comprises sending command functions and data to the analyzer unit by means of a wireless transceiver and antenna.

9. The method of claim 1 where refilling and replacing the reservoir of Avastin located in the analyzer unit further comprises refilling and replacing at least four drug ampoules coupled to the analyzer unit, wherein at least one of the four drug ampoules is for Avastin only.

10. A method for delivering Avastin into a brain tumor in a patient comprising:
    surgically implanting a multidelivery catheter beneath the skull and dura of the patient's brain into a treatment site;
    coupling the multidelivery catheter to an analyzer unit;
    operating the multidelivery catheter within the brain of the patient in order to infuse Avastin to the treatment site under control of the analyzer unit;
    suctioning in a sample of cerebral fluid from the treatment site and transferring it to the analyzer unit;
    tracking and monitoring the progress of the patient's treatment via the analyzer unit;
    altering and changing the patient's treatment by controlling the analyzer unit via an external controller communicated to the analyzer unit by an RF link, the external controller allowing proactive alteration of a delivery schedule of medicating agents to the brain of the patient by the cranium delivery pump based on measurements of a plurality of tumor parameters obtained from the cranium delivery pump and quantified by the analyzer unit;
    displaying the tumor parameter measurements on a display coupled to the external controller; and
    refilling and replacing a reservoir of Avastin located in the analyzer unit,
    wherein suctioning the sample of the patient's cerebral fluid further comprises suctioning the sample cerebral fluid at a variable rate into an intra-membrane reservoir defined between an outer and inner membrane of an inflatable balloon by the inflation and contraction of the inflatable balloon and a plurality of pores defined within the surface of the outer membrane and around each distal tip of a plurality of hollow needles coupled to the inner membrane.

11. The method of claim 10 where tracking and monitoring the progress of the patient's treatment via the analyzer unit further comprises displaying the amount of Avastin dispensed over time by the multidelivery catheter within the treatment site.

12. The method of claim 10 where tracking and monitoring the progress of the patient's treatment further comprises passing the sample of cerebral fluid through a lab-on-a-chip in the analyzer unit.

13. The method of claim 12 where passing the sample of cerebral fluid through a lab-on-a-chip further comprises measuring the effectiveness of intratumoral Avastin administration with the lab-on-a-chip.

14. The method of claim 13 where measuring the effectiveness of intratumoral Avastin administration further comprises displaying the results obtained from the lab-on-a-chip on a display.

15. The method of claim 10 further comprising providing a preoperative simulation of the infusion of Avastin and other intratumoral infusates to maximize efficiency and minimize toxicity by means of a diffusion model.

16. The method of claim 10 where altering and changing the patient's treatment by controlling the analyzer unit further comprises entering command functions and data into the analyzer unit from a remote keypad and displaying the commands on a display.

17. The method of claim 16 where altering and changing the patient's treatment by controlling the analyzer unit further comprises sending command functions and data to the analyzer unit by means of a wireless transceiver and antenna.

18. The method of claim 10 where refilling and replacing the reservoir of Avastin located in the analyzer unit further comprises refilling and replacing at least four drug ampoules coupled to the analyzer unit, wherein at least one of the four drug ampoules is for Avastin only.

* * * * *